(12) United States Patent
Nagano et al.

(10) Patent No.: US 9,417,163 B2
(45) Date of Patent: Aug. 16, 2016

(54) ANALYZER FOR SUBSTANCE

(71) Applicant: Hitachi, Ltd., Tokyo (JP)

(72) Inventors: Hisashi Nagano, Tokyo (JP); Yasuaki Takada, Tokyo (JP); Yuichiro Hashimoto, Tokyo (JP); Masakazu Sugaya, Tokyo (JP); Hideo Kashima, Tokyo (JP); Koichi Terada, Tokyo (JP); Yasutaka Suzuki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 259 days.

(21) Appl. No.: 14/191,622

(22) Filed: Feb. 27, 2014

(65) Prior Publication Data

US 2014/0260542 A1      Sep. 18, 2014

(30) Foreign Application Priority Data

Mar. 12, 2013 (JP) ................................. 2013-048714

(51) Int. Cl.
  *G01N 1/22*    (2006.01)
  *G01N 33/00*   (2006.01)
  *G01N 15/00*   (2006.01)
  *H01J 49/04*   (2006.01)

(52) U.S. Cl.
  CPC .......... *G01N 1/2211* (2013.01); *G01N 33/0057* (2013.01); *G01N 2015/0046* (2013.01); *H01J 49/0422* (2013.01)

(58) Field of Classification Search
  CPC .................................................. G01N 1/2211
  See application file for complete search history.

(56) References Cited

U.S. PATENT DOCUMENTS 3,759,617 A * 9/1973 Barringer ............. G01N 1/2211
                                                              356/315
5,800,579 A * 9/1998 Billingsley ............. B01D 45/16
                                                                55/337

FOREIGN PATENT DOCUMENTS

| JP | 50-094555 A | 7/1975 |
| JP | 52-107193 U | 8/1977 |
| JP | 05-026790 A | 2/1993 |
| JP | 07-284624 A | 10/1995 |
| WO | 2012/063796 A1 | 5/2012 |

OTHER PUBLICATIONS

Office Action, mailed May 24, 2016, which issued during the prosecution of Japanese Patent Application No. 2013-048714, which corresponds to the present application.

* cited by examiner

*Primary Examiner* — Paul West
(74) *Attorney, Agent, or Firm* — Baker Botts L.L.P.

(57) ABSTRACT

Provided is an analyzer for a substance, including: a first particle holding unit having a tubular shape; a first intake pipe for sucking a gas from an upper side of the first particle holding unit to cause a cyclonic phenomenon inside the first particle holding unit; a first supply pipe for supplying a sample containing particles, the first supply pipe being connected to a side surface of the first particle holding unit; a first flow control unit for controlling a flow rate of a gas flowing into the first particle holding unit to hold the rotationally moving particles inside the first particle holding unit for a predetermined time period and then cause the particles to settle, the first flow control unit being connected to a lower part of the first particle holding unit; a first collection heating unit for collecting and heating the settled particles; and an analysis unit for analyzing a substance vaporized from the particles through the heating by the first collection heating unit, the analysis unit being connected to the first collection heating unit through a pipe.

8 Claims, 16 Drawing Sheets

ANALYZER FOR SUBSTANCE

CLAIM OF PRIORITY

The present application claims priority from Japanese patent application JP2013-48714 filed on Mar. 12, 2013, the content of which is hereby incorporated by reference into this application.

BACKGROUND

This invention relates to an analyzer and method for collecting particles and analyzing a substance obtained from the particles.

Analysis of a substance in a gas or particles has been required in an engineering field and an environmental field. In particular, the environmental field requires an analyzer for measuring, with high sensitivity, a gas or floating particles in air rapidly or in real time to confirm the state of environmental pollution. Further, the engineering field requires, in a production process or quality control, an analyzer for measuring, with high sensitivity, a gas component or a particle component rapidly or in real time.

For example, International Patent WO2012/063796 discloses a method of analyzing particles in real time while collecting the particles continuously. In this method, a subject places his/her hand or an IC card over an authentication plane so that air is jetted thereto. Thus, explosive particles adhering to the hand or the IC card are separated to be sucked through a sampling port, and are collected by means of a cyclonic phenomenon to be analyzed in real time. This method enables rapid detection of particles, but in a case of a trace component, the sensitivity of an analysis unit may be insufficient.

The related art has a problem in that, when the substance obtained from the collected particles is intended to be analyzed rapidly or in real time, the sensitivity for detecting a low-concentration sample is insufficient.

SUMMARY

An aspect of the invention is an analyzer for a substance, including: a first particle holding unit having a tubular shape; a first intake pipe for sucking a gas from an upper side of the first particle holding unit to cause a cyclonic phenomenon inside the first particle holding unit; a first supply pipe for supplying a sample containing particles, the first supply pipe being connected to a side surface of the first particle holding unit; a first flow control unit for controlling a flow rate of a gas flowing into the first particle holding unit to hold the rotationally moving particles inside the first particle holding unit for a predetermined time period and then cause the particles to settle, the first flow control unit being connected to a lower part of the first particle holding unit; a first collection heating unit for collecting and heating the settled particles; and an analysis unit for analyzing a substance vaporized from the particles through the heating by the first collection heating unit, the analysis unit being connected to the first collection heating unit through a pipe.

According to an embodiment of the invention, it is possible to appropriately detect the substance from the particles collected in a low-concentration sample, and to analyze the substance rapidly or in real time. Other objects, configurations, and effects will become apparent from the following description of exemplary embodiments.

DETAILED DESCRIPTION OF THE EMBODIMENTS

Figure 1:
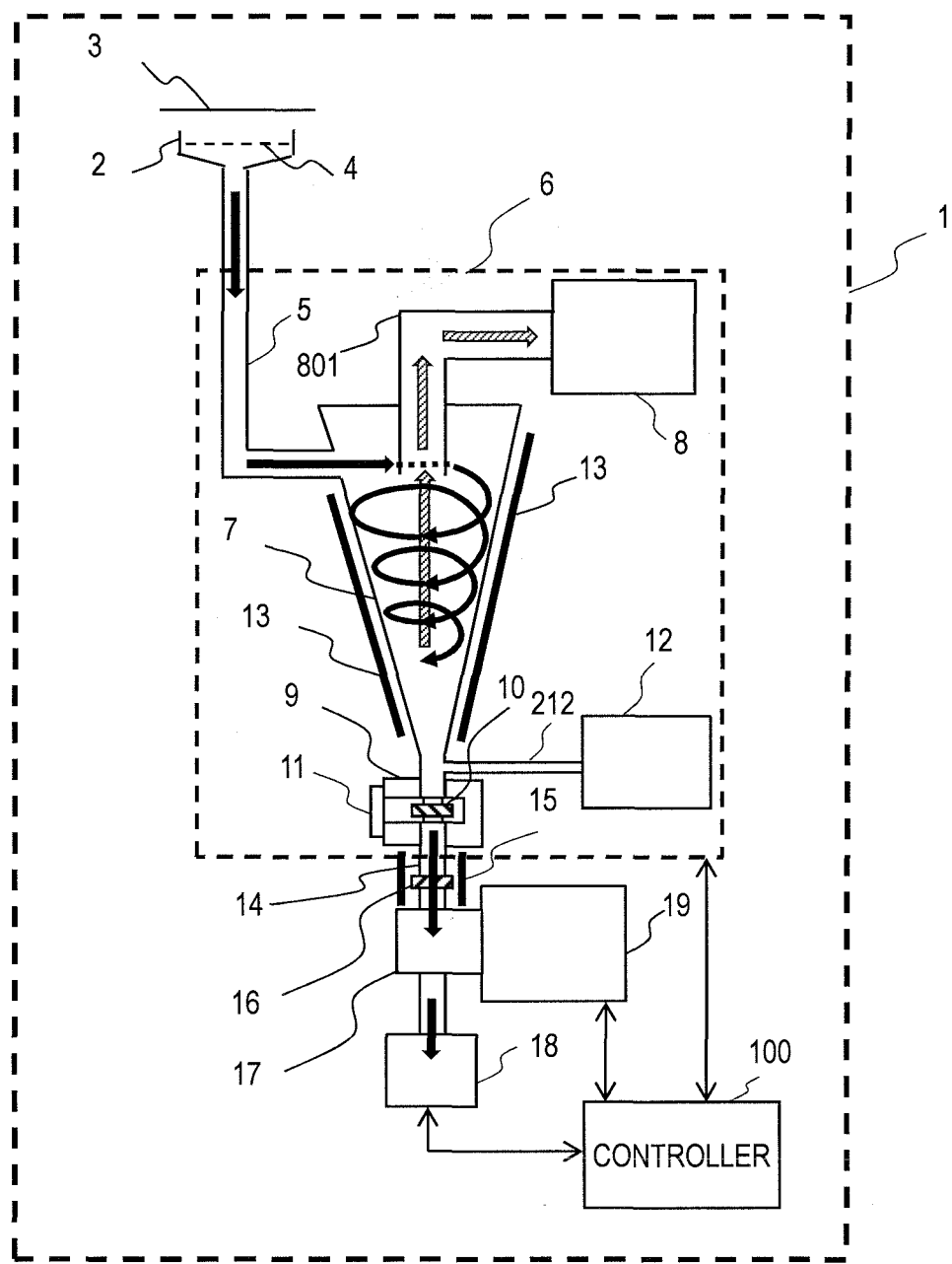
FIG. 1 is a schematic view illustrating one configuration example of an analyzer according to a first embodiment of this invention.

Now, embodiments of this invention are described in detail with reference to the drawings. It should be noted that details of an apparatus configuration and a processing operation described herein are examples for embodying this invention, and this invention also encompasses modified examples obtained through combination and substitution with a known technology.

In the embodiments of this invention, particles are collected and rotationally held in a space for a specific time period so as to condense the particles, and a substance is vaporized from the condensed particles so as to analyze the substance. For example, in a real-time analysis, a trace component has low concentration, and hence its analysis is difficult. In the embodiments of this invention, the internal pressure of a particle holding unit is changed by a flow control unit so as to condense and hold, in a rotating state, the collected particles each having a specific particle diameter size or more. With this, the substance can be acquired from the condensed particles to be analyzed.

First Embodiment

Now, a first embodiment of this invention is described. FIG. 1 is a schematic view illustrating an example of an analyzer of this embodiment. FIG. 1 illustrates an example of a method of collecting a gas and/or particle component in air by the analyzer installed indoors or outdoors. An analyzer 1 includes a sampling port 2, and a cover 3 for preventing rain, insects, or the like from entering the sampling port 2. The analyzer 1 sucks a gas and/or particles in air, which correspond to a substance to be detected, through the sampling port 2.

For example, the sampling port 2 is provided with a rough mesh filter 4 so as to prevent large dust, a finger, dirt, and the like from entering the sampling port 2. As an example of the rough mesh filter 4, a wire mesh (having, for example, an opening of 0.5 millimeter and an open area of 50%) can be used. This rough mesh filter 4 is replaceable, and when the rough mesh filter 4 is clogged with dust, a user can clean and reuse the rough mesh filter 4, or replace the rough mesh filter 4 with a new one.

The sucked gas and/or particles in air are introduced into a particle sampling unit 6 through an intake pipe 5. The particle sampling unit 6 includes a hollow conical particle holding unit 7, a large intake pump 8, a collection heating unit 9, a particle collection filter 10, a filter holder 11, a flow control unit 12, and an anti-adsorption device 13. The analyzer 1 includes a controller 100, and the controller 100 controls the respective components inside the particle sampling unit 6 and other components.

In the example of FIG. 1, the central axis of the hollow conical particle holding unit 7 is directed in a vertical direction. In a cross section perpendicular to the central axis, a side wall of the hollow conical particle holding unit 7 is shaped into a perfect circle (having a constant distance (radius) from the central axis). Depending on the design, the side wall may be shaped into a circle other than the perfect circle. The diameter of the particle holding unit 7 gradually decreases from the upper side toward the lower side. The large intake pump 8 sucks air from an upper side of the particle holding unit 7. In the example of FIG. 1, an intake pipe 801 of the large intake pump 8 is inserted into the particle holding unit 7 from a top surface of the particle holding unit 7. In a region other than an opening for the intake pipe 801, the top surface of the particle holding unit 7 is hermetically sealed.

The intake pipe 5 is connected to a tapered side wall of the particle holding unit 7. In an inner side surface of the particle holding unit 7, a center of a discharge port (sample introducing port to the particle holding unit 7) of the intake pipe 5 is positioned above a center of an intake port at a leading end of the intake pipe 801. The positional relationship therebetween depends on the design.

The large intake pump 8 sucks air at a flow velocity of, for example, 40 meters per minute. The suction causes a cyclonic phenomenon inside the conical particle holding unit 7. The cyclonic phenomenon more suitably occurs in the conical particle holding unit 7. In the cyclonic phenomenon, air at the center flows upward to be discharged through the intake pipe 801. Air on the outer peripheral side flows downward while being rotated. For example, particles each having a particle diameter of 1 micrometer or more rotationally move inside the particle holding unit 7, and are separated by the centrifugal force toward the outer periphery inside the particle holding unit 7. The rotation radius decreases toward the lower side. Other particles are discharged together with the air flow by the large intake pump 8 through the central intake pipe 801.

The minimum particle diameter (separation limit particle diameter) of the particles to be separated from the air flow by the rotational movement depends on the design of the particle sampling unit 6. The separation limit particle diameter changes depending on, for example, the maximum diameter of the particle holding unit 7, the cone angle, the height of the particle holding unit 7, the size of the discharge port of the intake pipe 5, the flow velocity caused by the large intake pump 8, and the like.

The particle sampling unit 6 introduces, by the large intake pump 8, a large volume of air into the particle holding unit 7. However, the sucked air is discharged outside the particle holding unit 7 by the large intake pump 8, and hence it is possible to prevent the sample of the substance to be detected from being diluted by the sucked air. With this, only particles of the substance to be detected having a specific particle diameter size (for example, particles of 1 micrometer or more) can be collected.

The large intake pump 8 can control the flow rate or the flow velocity. The large intake pump 8 may constantly operate in a constant suction amount. Alternatively, the large intake pump 8 may normally stop or operate in a small suction amount and, when the sample is sucked from outside, generate a necessary suction amount.

In a normal cyclonic separating apparatus, particles each having a particle diameter of 1 micrometer or more, which are sucked by the large intake pump 8, are separated toward the outer periphery by the centrifugal force to directly settle on the collection heating unit 9 provided at the bottom inside the particle holding unit 7.

However, in this configuration, on the lower side of the particle holding unit 7, the flow control unit 12 controls the flow rate of the air flowing into the particle holding unit 7. For example, the flow control unit 12 introduces, after a cyclonic phenomenon (rotational air flow) occurs inside the particle holding unit 7, air at a predetermined flow rate into the particle holding unit 7 through an intake pipe 212 (increases the flow rate of air flowing into the particle holding unit 7). When the flow rate of air flowing into the particle holding unit 7 increases, the pressure in the lower part of the particle holding unit 7 increases. When the flow rate of air flowing into the particle holding unit 7 decreases, the pressure in the lower part of the particle holding unit 7 decreases.

In the example of FIG. 1, the intake pipe 212 for introducing air for pressure adjustment is connected to a side surface of the particle holding unit 7 in the vicinity of the lower end thereof, and an opening of the intake pipe 212 on an inner side surface of the particle holding unit 7 is positioned immediately above the collection heating unit 9.

The flow control unit 12 adjusts the pressure immediately above the collection heating unit 9 to be higher than the pressure obtained when the cyclonic phenomenon occurs, or to be a zero pressure (atmospheric pressure) or a positive pressure (pressure higher than the atmospheric pressure). With this, the particles each having a particle diameter of 1 micrometer or more are, without being settled, held and condensed while being rotationally moved inside the particle holding unit 7.

For example, the flow control unit 12 includes a flow control valve, and by controlling the degree of valve opening, the flow control unit 12 controls the flow rate of air flowing into the particle holding unit 7. By increasing and decreasing the degree of valve opening, the flow rate of air flowing into the particle holding unit 7 increases and decreases, and the pressure immediately above the collection heating unit 9 increases and decreases. The flow control valve is, for example, a leak valve. Alternatively, the flow control unit 12 may include a pump so that air pressurized at a pressure higher than the atmospheric pressure is introduced into the particle holding unit 7.

The vertical position of the opening of the intake pipe 212 inside the particle holding unit 7 is located, for example, between the collection heating unit 9 and the lowermost position of the particles rotating by the cyclonic phenomenon. The intake pipe 212 may be protruded toward the center inside the particle holding unit 7 as long as the intake pipe 212 does not inhibit the settling of the particles on the collection heating unit 9.

The anti-adsorption device 13 heats and/or vibrates the particle holding unit 7 so as to prevent the particles from being adsorbed inside the particle holding unit 7. The vibration may be applied with use of an ultrasonic transducer, an eccentric motor, a vibrating motor, or the like. The particle holding unit 7 may be heated with use of a heater. The size of the particle holding unit 7 is determined depending on the particle diameter of the particles to be held and the suction flow velocity. In the example described herein, the shape of the particle holding unit 7 is determined so that the particle holding unit 7 can hold particles each having a particle diameter of 1 micrometer or more.

The particles each having a particle diameter of 1 micrometer or more are held and condensed for a predetermined time period (time period defined in advance) while being rotationally moved inside the particle holding unit 7. After that, the flow control unit 12 reduces the flow rate of air flowing into the particle holding unit 7 to reduce the pressure in the lower part. For example, the flow control unit 12 adjusts the pressure immediately above the collection heating unit 9 to be equal to or lower than the pressure when the cyclonic phenomenon occurs. As described above, for example, the flow control unit 12 reduces the degree of valve opening of the flow control valve to reduce the pressure inside the particle holding unit 7.

Through pressure adjustment by the flow control unit 12, the particles each having a particle diameter of 1 micrometer or more, which have been held and condensed while being rotationally moved, settle and adhere to the particle collection filter 10 provided inside the filter holder 11 of the collection heating unit 9. For example, the collection heating unit 9 constantly heats the particle collection filter 10. The collection heating unit 9 heats and vaporizes the collected particles.

The collection heating unit 9 heats the particles at, for example, 200° C. The temperature of the collection heating unit 9 may be any temperature that can vaporize the collected particles, and the temperature of the collection heating unit 9 may be changed depending on the target particle component and gas component. The particle collection filter 10 may be, for example, a stainless steel wire filter or a sintered filter having a filtration accuracy of 1 micrometer.

A user can take out the particle collection filter 10 from the filter holder, and can clean and reuse the particle collection filter 10 or replace the particle collection filter 10 with a new one as necessary. The particle collection filter 10 may be manually replaced, or may be replaced by an automatic replacing apparatus. The particle collection filter 10 may be any filter having a filtration accuracy that can capture a particle having a particle diameter of 1 micrometer or more. For example, a stainless steel wire filter having a filtration accuracy of 1 micrometer to 50 micrometers can be used.

An analysis pipe 14 is connected to a back surface of the particle collection filter 10 of the collection heating unit 9. The heated particles are vaporized to be introduced into an ion source 17 by an intake pump 18 through the analysis pipe 14. For example, the intake pump 18 sucks air at a flow rate of 2.0 liters per minute. An analysis pipe heater 15 heats the analysis pipe 14 to prevent a gas from being adsorbed inside the analysis pipe.

For example, the analysis pipe heater 15 heats the analysis pipe 14 at 180° C. The analysis pipe 14 and the analysis pipe heater 15 may be shortened as much as possible, or those members may be omitted to directly connect the collection heating unit 9 and the ion source 17 to each other. The analysis pipe 14 is provided with a fine mesh filter 16 so as to prevent the ion source 17 from being stained by particles that have not been vaporized in the collection heating unit 9.

The fine mesh filter 16 may be, for example, a stainless steel wire filter or a sintered filter having a filtration accuracy of 1 micrometer. The user can clean and reuse the fine mesh filter 16 or replace the fine mesh filter 16 with a new one as necessary.

The ion source 17 is an atmospheric pressure chemical ionization source that uses negative corona discharge or positive corona discharge.

Ions may be generated by other methods such as radiation exposure by a radiation source, irradiation of electrons, light, or laser light, penning discharge, glow discharge, barrier discharge, and electrospray.

This embodiment utilizes ionization by an ion source, but other analysis methods that do not utilize an ion source may be used, such as analysis methods that involve directly introducing the substance into gas chromatography (GC), liquid chromatography (LC), and high performance liquid chromatography (HPLC), analysis methods that utilize various light sources such as fluorescence, infrared rays, and ultraviolet rays, and related-art analysis methods that involve measurement of the weight and particles. The vaporized component may be analyzed by any method as long as the method utilizes rotating air flow to rotationally hold and condense the particles.

An analysis unit 19 subjects ions generated from the sample by the ion source 17 to mass spectrometry. As the analysis unit 19, for example, a wire-type linear ion trap mass spectrometer may be used. As a method for mass spectrometry, linear ion trap mass spectrometry, quadrupole ion trap mass spectrometry, quadrupole filter mass spectrometry, triple quadrupole mass spectrometry, time-of-flight mass spectrometry, magnetic sector mass spectrometry, ion mobility mass spectrometry, and the like may be utilized. The analysis unit 19 measures the mass spectrum to identify the component of the particles and determine the concentration thereof based on the mass spectrum.

Figure 2:
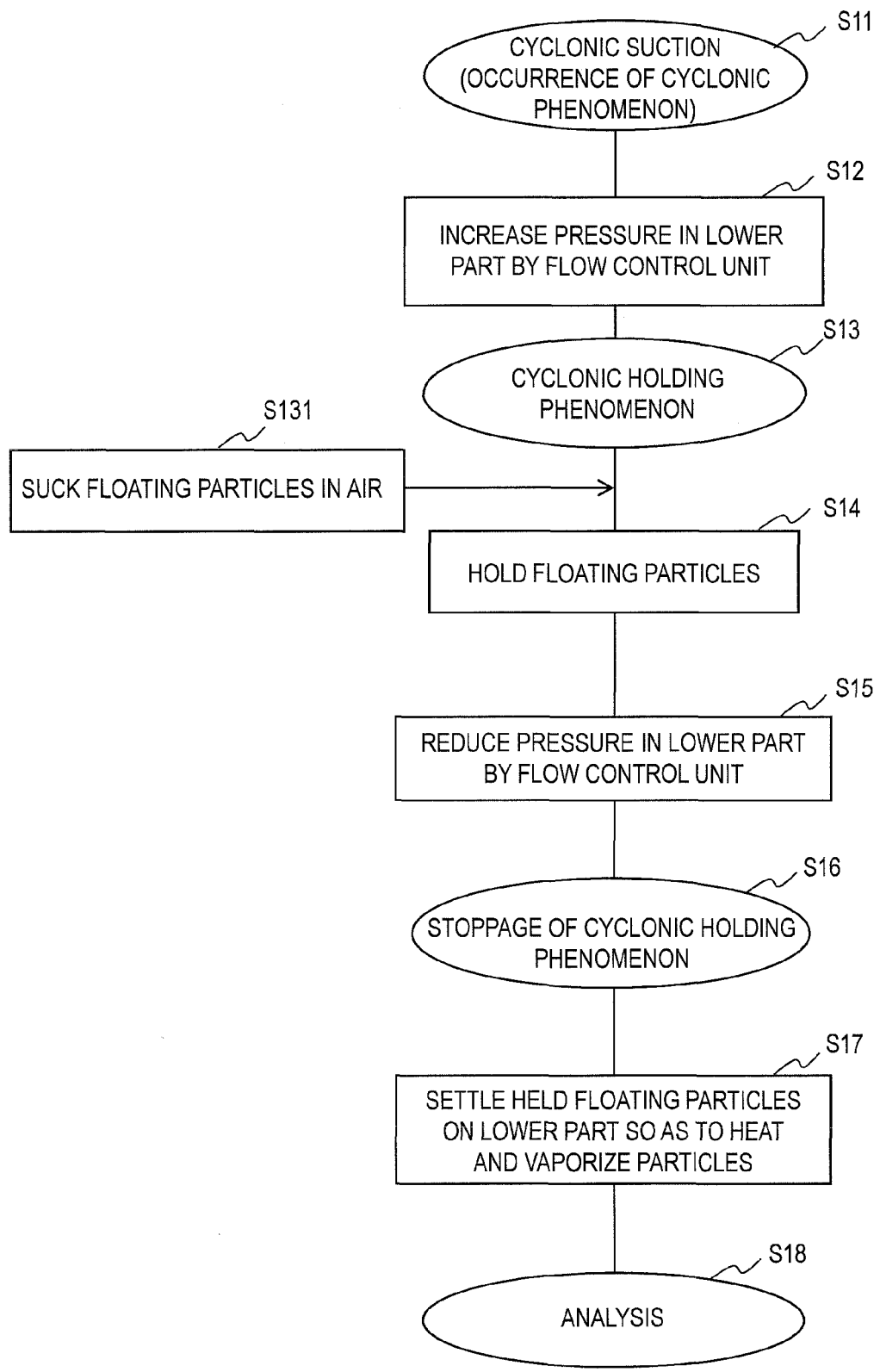
FIG. 2 is a flow chart illustrating an example of a processing procedure for particle analysis according to the first embodiment.
Figure 3A:
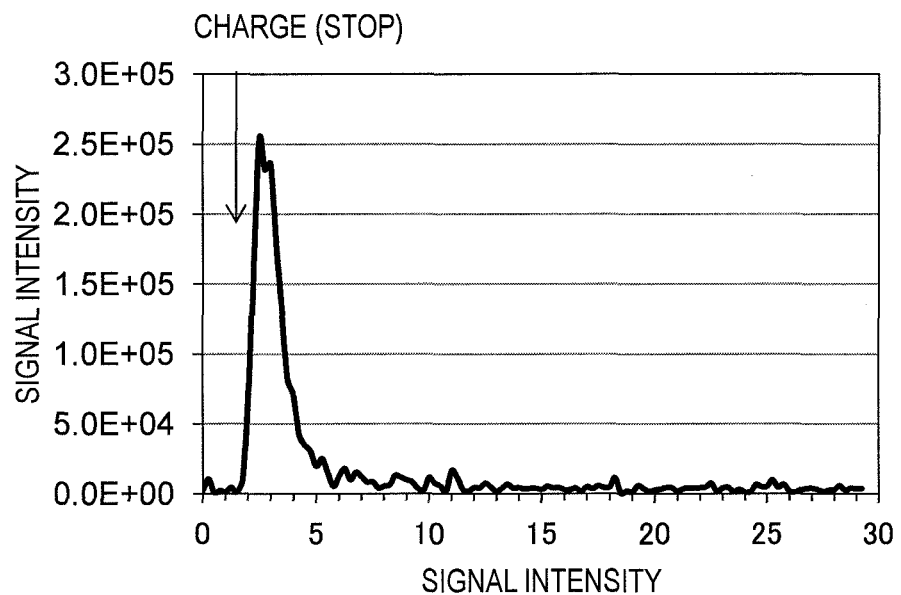
FIG. 3A is a graph showing an example of a temporal profile of a mass spectrum of trinitrotoluene measured by the analyzer according to the first embodiment.
Figure 3B:
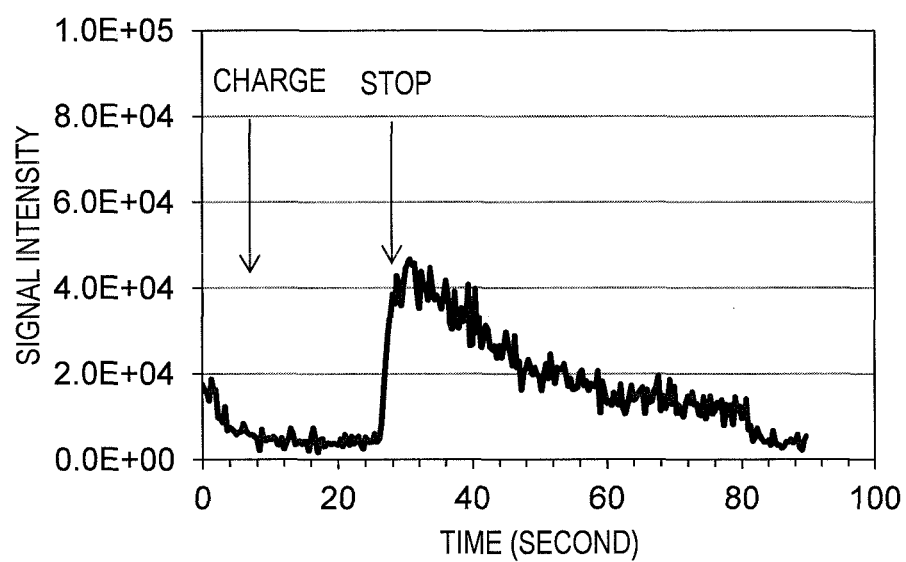
FIG. 3B is a graph showing an example of a temporal profile of a mass spectrum of trinitrotoluene measured by the analyzer according to the first embodiment.
Figure 4A:
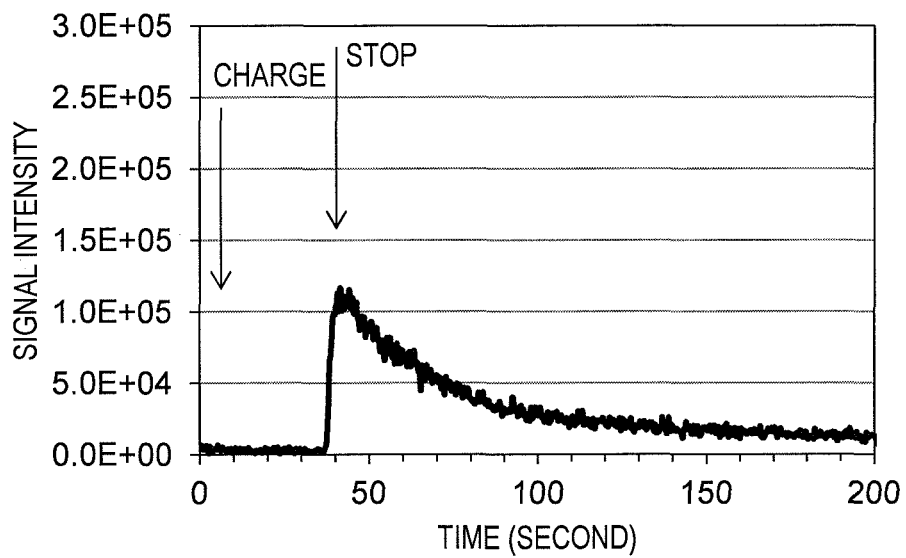
FIG. 4A is a graph showing an example of a temporal profile of a mass spectrum of trinitrotoluene measured by the analyzer according to the first embodiment in a case where a charging amount is changed.
Figure 4B:
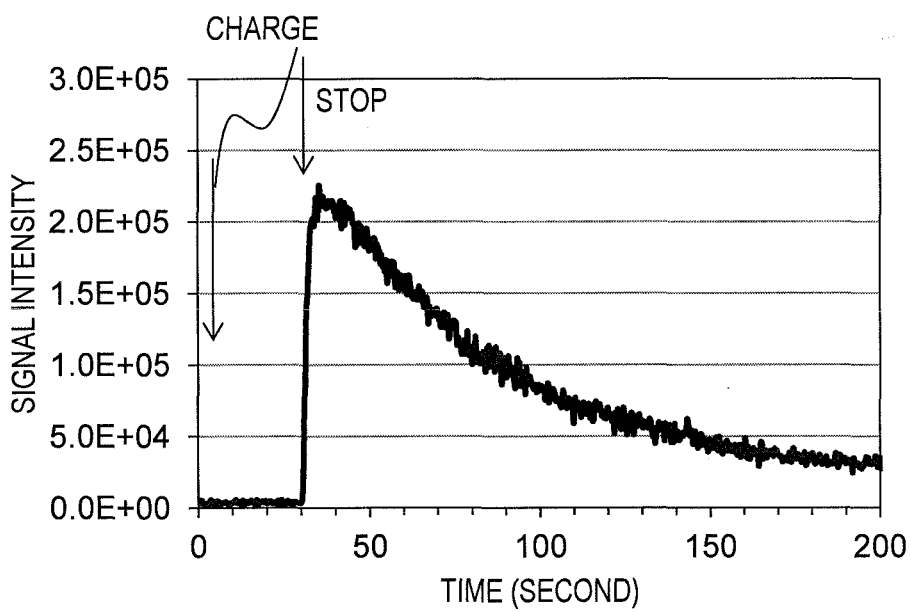
FIG. 4B is a graph showing an example of a temporal profile of a mass spectrum of trinitrotoluene measured by the analyzer according to the first embodiment in a case where the charging amount is changed.

FIG. 2 is a flow chart illustrating an example of a processing procedure for the particle analysis according to this embodiment. First, the large intake pump 8 starts suction, and then gas rotational movement corresponding to a cyclonic phenomenon occurs inside the particle holding unit 7 (Step S11).

Figure 5:
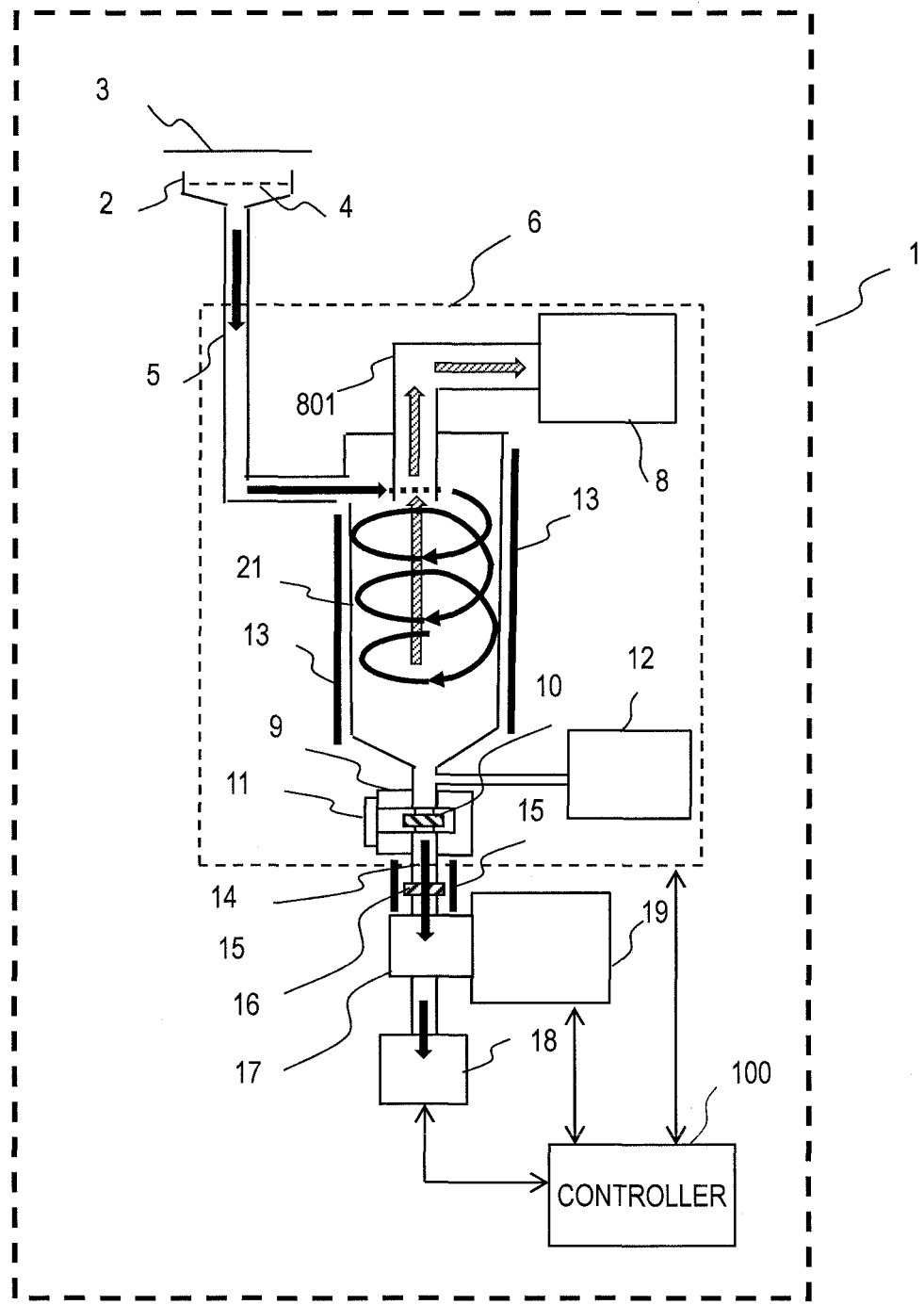
FIG. 5 is a schematic view illustrating an example of an analyzer including a cylindrical particle holding unit according to the first embodiment.

After that, the flow control unit 12 increases, in accordance with an instruction from the controller 100, the flow rate of air flowing into the particle holding unit 7 (for example, increases the degree of valve opening from zero to a predetermined value), to thereby increase the pressure in the lower part (Step S12). With this, a phenomenon that particles each having a predetermined particle diameter or more are held while being rotationally moved occurs inside the particle holding unit 7 (Step S13). The particle sampling unit 6 sucks, through suction of the large intake pump 8, air containing a gas and/or particles corresponding to the substance to be detected through the sampling port 2 (Step S131).

The particle holding unit 7 holds, among the floating particles in the sucked air, particles having a specific particle diameter size (for example, particles each having a particle diameter of 1 micrometer or more) while rotating the particles in a space inside the particle holding unit 7 (Step S14). After holding the particles for a predetermined time period, the flow control unit 12 decreases, in accordance with an instruction from the controller 100, the flow rate of air flowing into the particle holding unit 7 (for example, decreases the degree of valve opening to zero), to thereby reduce the pressure in the lower part (Step S15). With this, the phenomenon that the particles are held inside the particle holding unit 7 stops (Step S16).

The particles having a specific particle diameter size that have been rotationally held substantially simultaneously settle on the lower part of the particle holding unit 7, and the particles are collected by the particle collection filter 10 of the collection heating unit 9. The collection heating unit 9 heats and vaporizes the particles adhering to the particle collection filter 10 (Step S17). The analysis unit 19 analyzes the vaporized component (Step S18).

The inventors of this invention used an analyzer to which this embodiment was applied to actually measure trinitrotoluene corresponding to a typical substance of military explosive components. FIGS. 3A and 3B show examples of measurement results of the analyzer. FIGS. 3A and 3B show temporal profiles of the mass spectrum of trinitrotoluene.

FIG. 3A shows measurement results of a case where the flow control unit 12 does not control the pressure and the particles rotating inside the particle holding unit 7 are not held and condensed. FIG. 3B shows measurement results of a case where the flow control unit 12 increases the pressure in the lower part of the particle holding unit 7 to hold the particles for a predetermined time period inside the particle holding unit 7.

The sample used was silica gel particles containing trinitrotoluene and each having a particle diameter of 20 micrometers to 30 micrometers. The content of trinitrotoluene in this sample was 0.1%. The sample used was about 50 micrograms, and the content of trinitrotoluene was about 50 nanograms. The sample was charged through the sampling port 2 for measurement.

The particle holding unit 7 held and condensed the sucked particles while rotating the particles. Through the pressure control (pressure reduction) by the flow control unit 12, the particles that had rotationally moved settled on the collection heating unit 9. The collection heating unit 9 heated and vaporized the particles. The ion source 17 ionized heated and vaporized trinitrotoluene, and the analysis unit 19 analyzed the mass of the ionized substance through negative ion detection. The temperature of the particle collection filter 10 in the collection heating unit 9 was 200° C., and the temperature of each of the analysis pipe heater 15 and the ion source 17 was 180° C.

Trinitrotoluene has a molecular weight (M) of 227. FIGS. 3A and 3B show temporal profiles in a mass-to-charge ratio m/z of 227. The measurement results of FIG. 3A represent that, simultaneously with the charge of the silica gel particles containing trinitrotoluene, particles collected in the particle holding unit 7 reach the collection heating unit 9 to be detected as a signal.

On the other hand, the measurement results of FIG. 3B represent that, after the charge of the silica gel particles containing trinitrotoluene, the flow control unit 12 controls the flow rate to increase the internal pressure of the particle holding unit 7, and the particles are held in a rotating state inside the particle holding unit 7.

Further, the measurement results of FIG. 3B represent that, after about 30 seconds, the flow control unit 12 reduces the internal pressure, and thus the particles that have been held inside the particle holding unit 7 settle and reach the collection heating unit 9 to be detected as a signal. As represented by the measurement results, a particle holdable time period is 0.1 second or more, and the maximum holdable time period changes depending on the size of the particle holding unit 7. It should be noted that the particles may be settled by stopping the large intake pump 8.

FIGS. 4A and 4B show examples of the temporal profiles of the mass spectrum of trinitrotoluene with respect to different charging amounts, which were measured with use of the analyzer 1 of this embodiment. FIG. 4A shows measurement results when the particles were charged by an amount corresponding to 3 times of charging. FIG. 4B shows measurement results when the particles were charged by an amount corresponding to 10 times of charging. As the sample, silica gel particles containing trinitrotoluene and each having a particle diameter of 20 micrometers to 30 micrometers were used, and the content of trinitrotoluene was 0.1%.

As the amount corresponding to 3 times of charging, about 150 micrograms of silica gel particles were charged, which corresponded to the trinitrotoluene content of about 150 nanograms. As the amount corresponding to 10 times of charging, about 500 micrograms of silica gel particles were charged, which corresponded to the trinitrotoluene content of about 500 nanograms.

In this measurement, after the silica gel particles containing trinitrotoluene were charged, the flow control unit 12 controlled the flow rate to increase the internal pressure of the particle holding unit 7. In this manner, the particles were held in a rotating state inside the particle holding unit 7. After about 30 seconds, the flow control unit 12 reduced the internal pressure, and thus the particles that had been held inside the particle holding unit 7 settled and reached the collection heating unit 9 to be detected as a signal. It should be noted that the particles may be settled by stopping the large intake pump 8.

As shown in FIGS. 4A and 4B, as the charging amount increased, the amount of particles to be held inside the particle holding unit 7 increased. As a result, it was confirmed that, through the flow rate control (control of the internal pressure of the particle holding unit 7) by the flow control unit 12, the particles were rotationally held inside the particle holding unit 7.

As described above, with the above-mentioned configuration, a substance can be appropriately detected from particles collected in a low-concentration sample, and can be analyzed rapidly or in real time.

FIG. 5 is a schematic view illustrating another configuration example of the analyzer according to this embodiment. This analyzer includes a cylindrical particle holding unit 21. This analyzer differs from the configuration illustrated in FIG. 1 in that the particle holding unit 21 of this analyzer has a cylindrical shape instead of a conical shape.

The central axis of the cylindrical particle holding unit 21 is directed in the vertical direction. In a cross section perpendicular to the central axis, a side wall of the cylindrical particle holding unit 21 is shaped into a perfect circle (having a constant distance (radius) from the central axis). Depending on the design, the side wall may be shaped into a circle other than the perfect circle. The diameter of the particle holding unit 21 is the same at any position in the vertical direction. Other points are similar to those in the configuration illustrated in FIG. 1, and the operation is also similar.

Figure 6:
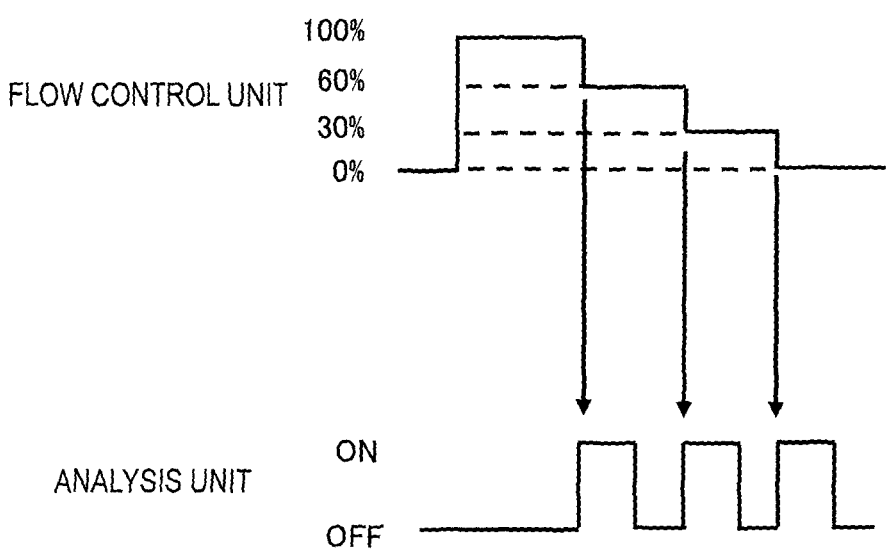
FIG. 6 is a diagram illustrating an example of a sequence of analyzing particles having different particle diameters through an operation of a flow control unit according to the first embodiment.

With reference to FIG. 6, there is given a description of an example of a sequence of individually analyzing particles in different particle diameter ranges through the operation of the flow control unit according to this embodiment. FIG. 6 illustrates changes of the operational signal of the flow control unit 12 and the operational signal of the analysis unit 19.

The operational signal of the flow control unit 12 corresponds to the flow rate of air flowing into the particle holding unit. As the value of the operational signal increases, the flow rate of air flowing into the particle holding unit increases, and when the operational signal is 0%, the flow rate is zero. For example, the operational signal of the flow control unit 12 represents the degree of valve opening. The operational signal of the analysis unit 19 represents whether or not the analysis unit 19 is analyzing a substance. When the operational signal is ON, the analysis unit 19 is analyzing a substance from the collection heating unit 9.

When the flow control unit 12 operates by 100%, particles each having a specific particle diameter or more are held inside the particle holding unit 7 while being rotationally moved. When the particles are rotationally held inside the particle holding unit 7, as the particles have a larger particle diameter, the particles are rotated and held on the upper side inside the particle holding unit 7. This is because the radius of rotation of particles caused by the cyclonic phenomenon reduces toward the lower side, and thus the acceleration toward the outer periphery increases. This point is similar also in the cylindrical particle holding unit 21.

After that, the flow control unit 12 changes the state of operation from 100% to 60%. The holding position of the rotationally-held particles moves downward. The particles each having a specific particle diameter or less settle on the collection heating unit 9, and adhere to the particle collection filter 10 inside the filter holder 11. The analysis unit 19 analyzes the substance heated and vaporized at the particle collection filter 10.

After the analysis unit 19 has ended the analysis, the flow control unit 12 changes the state of operation from 60% to 30%. The holding position of the rotationally-held particles moves downward. The particles each having a specific particle diameter or less settle on the collection heating unit 9, and adhere to the particle collection filter 10 inside the filter holder 11. The analysis unit 19 analyzes the substance heated and vaporized at the particle collection filter 10.

After the analysis unit 19 has ended the analysis, the flow control unit 12 changes the state of operation from 30% to 0%. All the rotationally-held particles settle on the collection heating unit 9, and adhere to the particle collection filter 10 inside the filter holder 11. The analysis unit 19 analyzes the substance heated and vaporized at the particle collection filter 10.

As described above, the flow control unit 12 reduces, in a stepwise manner, the flow rate of air flowing into the particle holding unit 7 so as to reduce, in a stepwise manner, the pressure in the lower part. As a result, particles in different particle diameter ranges can be collected by the collection heating unit 9 in each of the stages, and the analysis unit 19 can individually analyze the particles in different particle diameter ranges.

A measurement by way of the method illustrated in FIG. 6 was performed with use of the analyzer 1 having the configuration described with reference to FIG. 1. In the measurement, in a state where the flow control unit 12 operated by 60%, particles each having a particle diameter of about 1 micrometer to 5 micrometers were detected in the collection heating unit 9. In a state where the flow control unit 12 operated by 30%, particles each having a particle diameter of about 5 micrometers to 10 micrometers were detected in the collection heating unit 9. In a state where the flow control unit 12 operated by 0%, particles each having a particle diameter of about 10 micrometers or more were detected in the collection heating unit 9. As described above, in accordance with the flow rate controlled by the flow control unit 12, particles in different particle diameter ranges were able to be collected.

Second Embodiment

Figure 7:
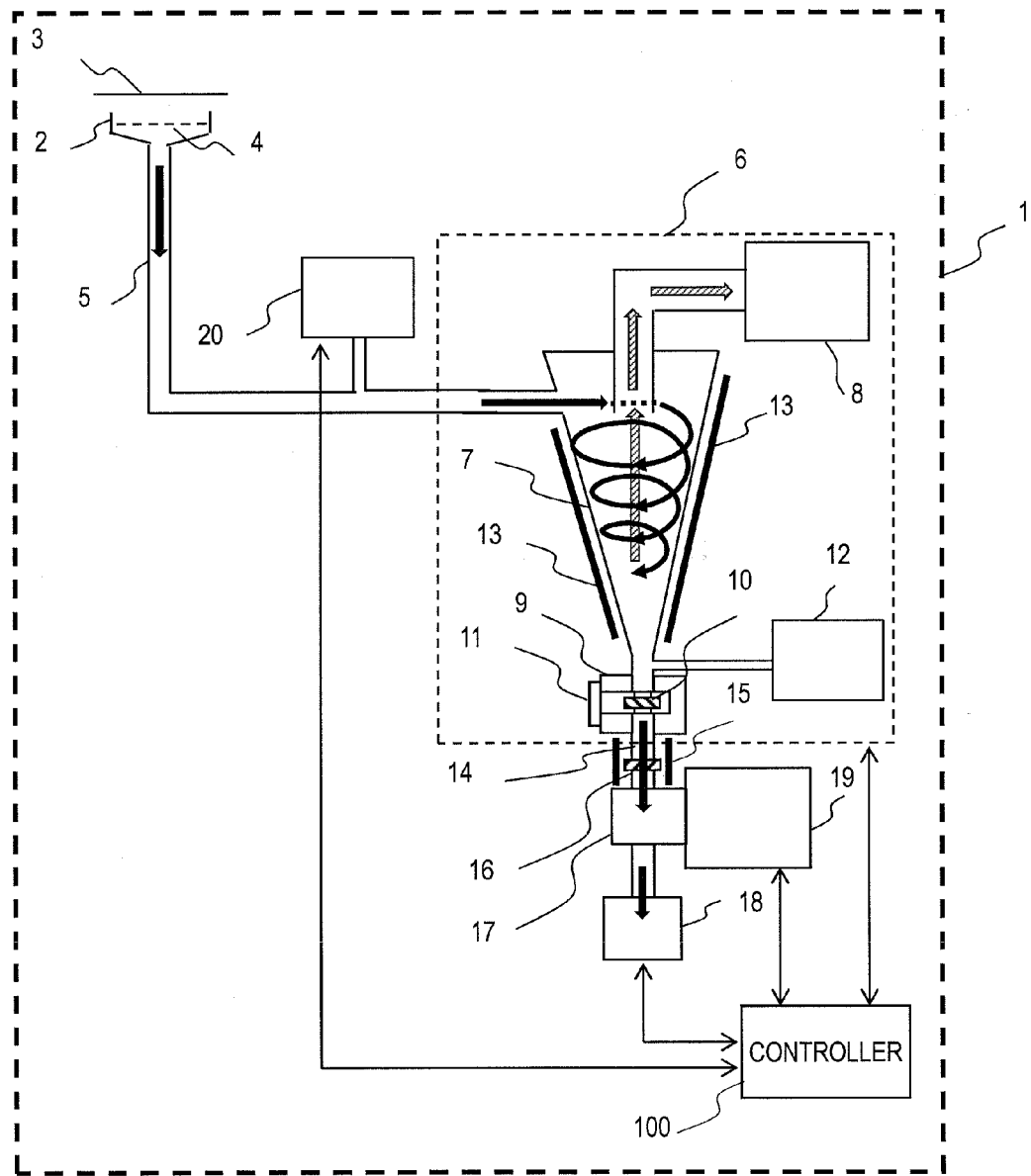
FIG. 7 is a schematic view illustrating an example of an analyzer for gas component analysis according to a second embodiment of this invention.

Now, a second embodiment of this invention is described. This embodiment represents an example of a method of measuring, with high sensitivity, not only a particle component but also a gas component in air. In the following, points different from the first embodiment are mainly described. FIG. 7 is a schematic view illustrating an example of an analyzer for gas component analysis according to this embodiment. This embodiment represents a method of collecting a gas and particle component in air by the analyzer installed indoors or outdoors. In particular, the analyzer of this embodiment can measure a gas component with high sensitivity.

The analyzer 1 includes, in the middle of the intake pipe 5, a supply unit 20 for supplying silica gel as an adsorbent. As the adsorbent, for example, silica gel particles each having a particle diameter of 20 micrometers to 30 micrometers can be used. The adsorbent may be made of any material that can adsorb the gas and/or particle component, and silica gel, glass beads, plastic beads, a gel material, or the like can be used. The supply unit 20 may be arranged at a position different from the position in the middle of the intake pipe 5. For example, the supply unit 20 may be arranged at the sampling port 2 or in the particle sampling unit 6.

The silica gel particles move similarly to the particles to be analyzed that are described in the first embodiment. The flow control unit 12 controls the pressure inside the particle holding unit 7, and hence silica gel particles each having a particle diameter of 1 micrometer or more, which are supplied from the supply unit 20 and sucked by the large intake pump 8, do not immediately settle but are held inside the particle holding unit 7 while being rotationally moved.

The silica gel particles supplied from the supply unit 20 are held inside the particle holding unit 7 while being rotationally moved. At this time, the sucked gas and/or particles in air are adsorbed to the silica gel particles, and are held by the silica gel particles for a predetermined time period in a condensed state.

After that, the flow control unit 12 adjusts the pressure in the lower part of the particle holding unit 7, and thus the silica gel particles that have rotationally moved in a space inside the particle holding unit 7 settle to be collected by the particle collection filter 10 inside the filter holder 11 of the collection heating unit 9. The collection heating unit 9 heats the silica gel particles on the particle collection filter 10.

The heating temperature in the collection heating unit 9 is, for example, 200° C. The temperature of the collection heating unit 9 may be any temperature that can vaporize the gas and/or particle component in air adsorbed to the silica gel particles to be collected, and may be changed depending on the target particle component and gas component.

The particle collection filter 10 may be any filter having a filtration accuracy that can capture the silica gel particles supplied from the supply unit 20. For example, a stainless steel wire filter or a sintered filter having a filtration accuracy of 1 micrometer to 50 micrometers can be used.

The gas and/or particle component in air adsorbed to the silica gel particles is heated to be vaporized. The vaporized sample is introduced into the ion source 17 by the intake pump 18 through the analysis pipe 14. For example, the intake pump 18 sucks air at a flow rate of 2.0 liters per minute. The analysis unit 19 measures the mass spectrum to identify the gas and/or particle component in air adsorbed to the silica gel particles and determine the concentration thereof based on the mass spectrum.

Figure 8:
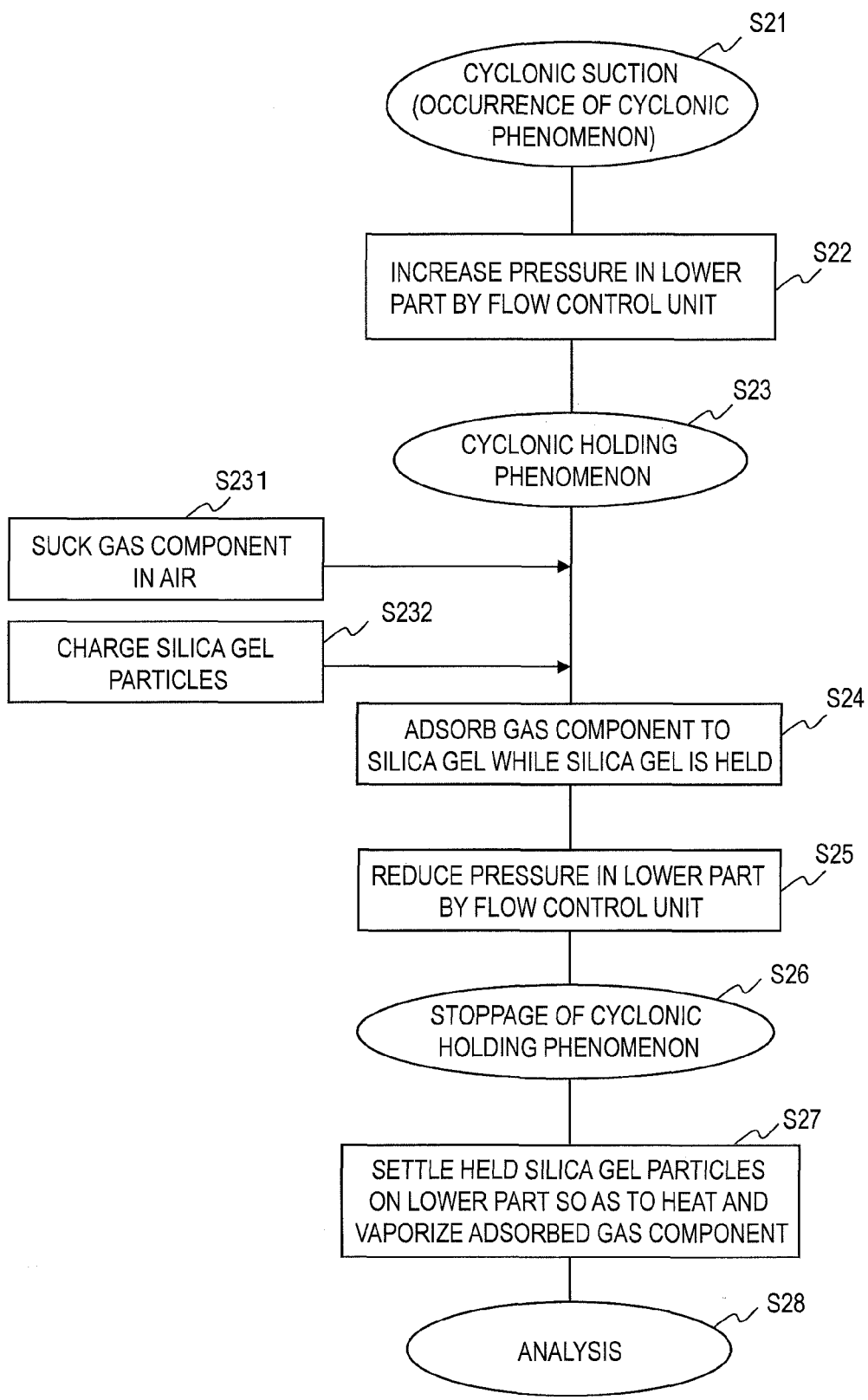
FIG. 8 is a flow chart illustrating an example of a processing procedure for the gas component analysis according to the second embodiment.

FIG. 8 is a flow chart illustrating an example of a procedure of component analysis according to this embodiment. The large intake pump 8 starts suction, and then gas rotational movement corresponding to a cyclonic phenomenon occurs inside the particle holding unit 7 (Step S21). After that, the flow control unit 12 increases, in accordance with an instruction from the controller 100, the pressure in the lower part of the particle holding unit 7 (Step S22). With this, a phenomenon that particles are held while being rotationally moved occurs inside the particle holding unit 7 (Step S23). The particle sampling unit 6 sucks, through suction of the large intake pump 8, the gas and/or particles in air corresponding to the substance to be detected through the sampling port 2 (Step S231).

The supply unit 20 supplies, in accordance with an instruction from the controller 100, silica gel particles for adsorbing the gas and/or particles in air (Step S232). The order of Step S231 and Step S232 may be reversed.

The particle holding unit 7 holds the silica gel particles each having a specific particle diameter or more, for example, a particle diameter of 1 micrometer or more, while rotating the particles in a space inside the particle holding unit 7. The gas and/or particles in air are adsorbed to the silica gel rotated and held inside the particle holding unit 7 (Step S24).

After holding the silica gel particles for a predetermined time period, the flow control unit 12 reduces, in accordance with an instruction from the controller 100, the pressure in the lower part of the particle holding unit 7 (Step S25). With this, the phenomenon that the silica gel particles are held inside the particle holding unit 7 stops (Step S26). The silica gel particles each having a specific particle diameter or more (for example, particles each having a particle diameter of 1 micrometer or more), which have been rotationally held, substantially simultaneously settle on the lower part of the particle holding unit 7, and the silica gel particles are collected by the particle collection filter 10 of the collection heating unit 9. The collection heating unit 9 heats the silica gel adhering to the particle collection filter 10 to vaporize the adsorbed gas and/or particle component (Step S27). The analysis unit 19 analyzes the vaporized component (Step S28).

As described above, this embodiment enables appropriate analysis of not only a particle component but also a gas component in air. Specifically, in this embodiment, the adsorbent particles are caused to adsorb a gas component while the adsorbent particles are rotationally held in a space, and are settled in a condensed state and heated to vaporize the adsorbed gas and/or particle component. With this, a trace gas component can be rapidly analyzed.

Third Embodiment

Figure 9:
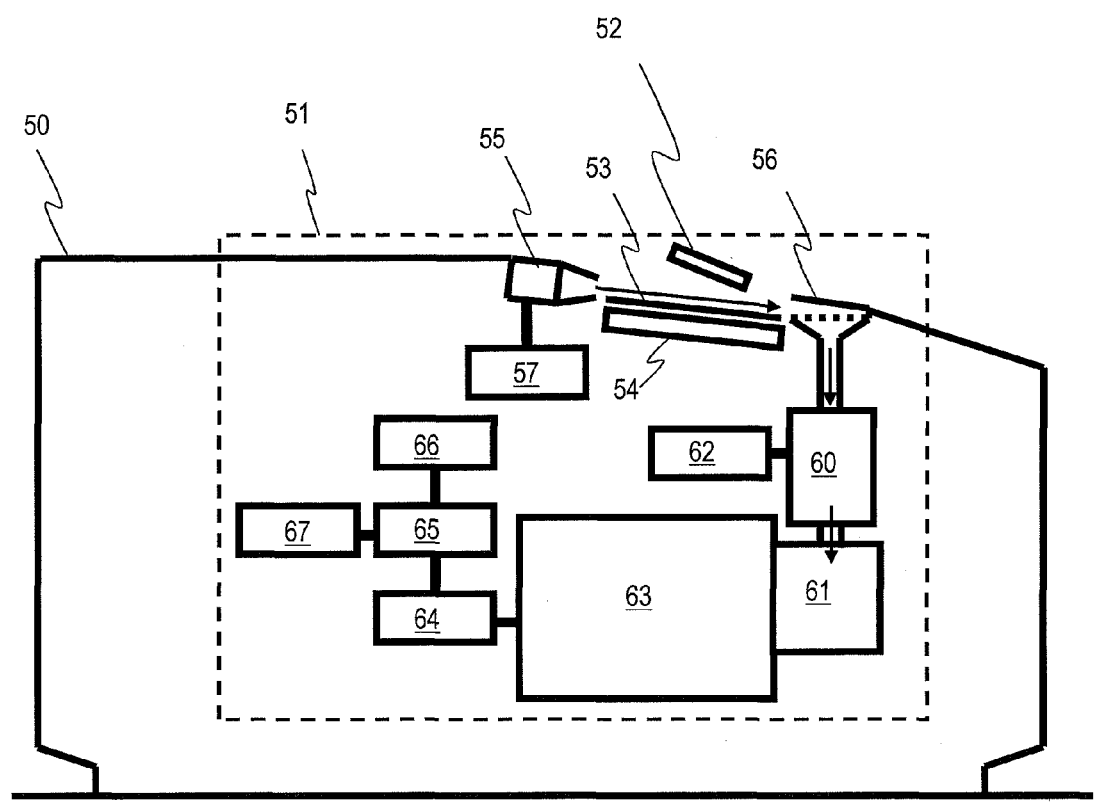
FIG. 9 is a schematic view illustrating an example of an analyzer embedded in a security gate according to a third embodiment of this invention.

Now, a third embodiment of this invention is described. This embodiment represents an example of a security gate incorporating a function of detecting explosive particles. FIG. 9 is a schematic view illustrating an example of an analyzer embedded in a security gate according to this embodiment. The analyzer of this embodiment is embedded in a security gate 50 installed at airports, stations, buildings, important facilities, and the like.

Instead of the security gate, the analyzer of this embodiment can be embedded in an automatic ticket gate at the station, a boarding gate at the airport, ship, or the like, a gate at the security checkpoint for carry-on baggage or checked baggage, an entrance and exit ticket gate at the amusement facility, or the like.

The security gate 50 has an analyzer 51 embedded therein. The analyzer 51 includes an authentication unit 54 for authenticating an authentication target 52 that is brought close to an authentication plane 53. The authentication target 52 may be, for example, an IC card, a cellular phone, a ticket, and in addition, biological parts such as a hand, a finger, and an eye. Further, the authentication target 52 may be an employee ID card and a temporary entrance and exit card. The analyzer 51 need not perform authentication processing. The person to be inspected places his/her hand or personal item, which is considered to have explosive particles adhering thereon, over the authentication plane without an operation for authentication.

In the example of FIG. 9, the analyzer 51 includes a blowing unit 55 for blowing air along the authentication plane 53. The air from the blowing unit 55 separates a gas and/or particles that are a substance to be detected, which adhere on the authentication target 52. A blowing control unit 57 controls a flow rate, a flow velocity, a jetting pressure, a temperature, a jetting time period, a jetting timing, or the like of the blowing unit 55.

An introduction unit 56 sucks the separated gas and/or particles as the substance to be detected. A particle sampling unit 60 holds and condenses the sucked particles (including gas adsorbent particles) as the substance to be detected. The particle sampling unit 60 maintains, through the operation of the flow control unit (not shown in FIG. 9) in the above-mentioned other embodiments, the rotational movement of the particles as the substance to be detected, and holds the particles for a predetermined time period in a condensed state. A collection filter control unit 62 controls operations such as suction flow rate, flow velocity, temperature, and operational sequence in the particle sampling unit 60.

The particles to be detected that have been held in a space inside the particle sampling unit 60 are settled through the operation of the flow control unit. The settled particles are heated and vaporized. An ion source 61 ionizes a vaporized gas. An analysis unit 63 analyzes the mass of the ionized substance. A data processor 64 controls the temperature, the voltage, and the operational sequence of each of the ion source 61 and the analysis unit 63 to acquire mass spectrum data.

A mass database unit 66 stores the mass spectrum data derived from the substance to be detected. An identification unit 65 compares the mass spectrometry result of the sample obtained by the analysis unit 63 with the mass spectrum data stored in the mass database unit 66 to determine presence and absence of the substance to be detected.

A monitor 67 displays the presence and absence of the substance to be detected and/or the analysis result. Based on the result displayed on the monitor 67, the security gate 50 carries out operations such as alarm indication, gate closure, notification to a monitoring center, recording by a security camera, and storage of authentication data.

Figure 10:
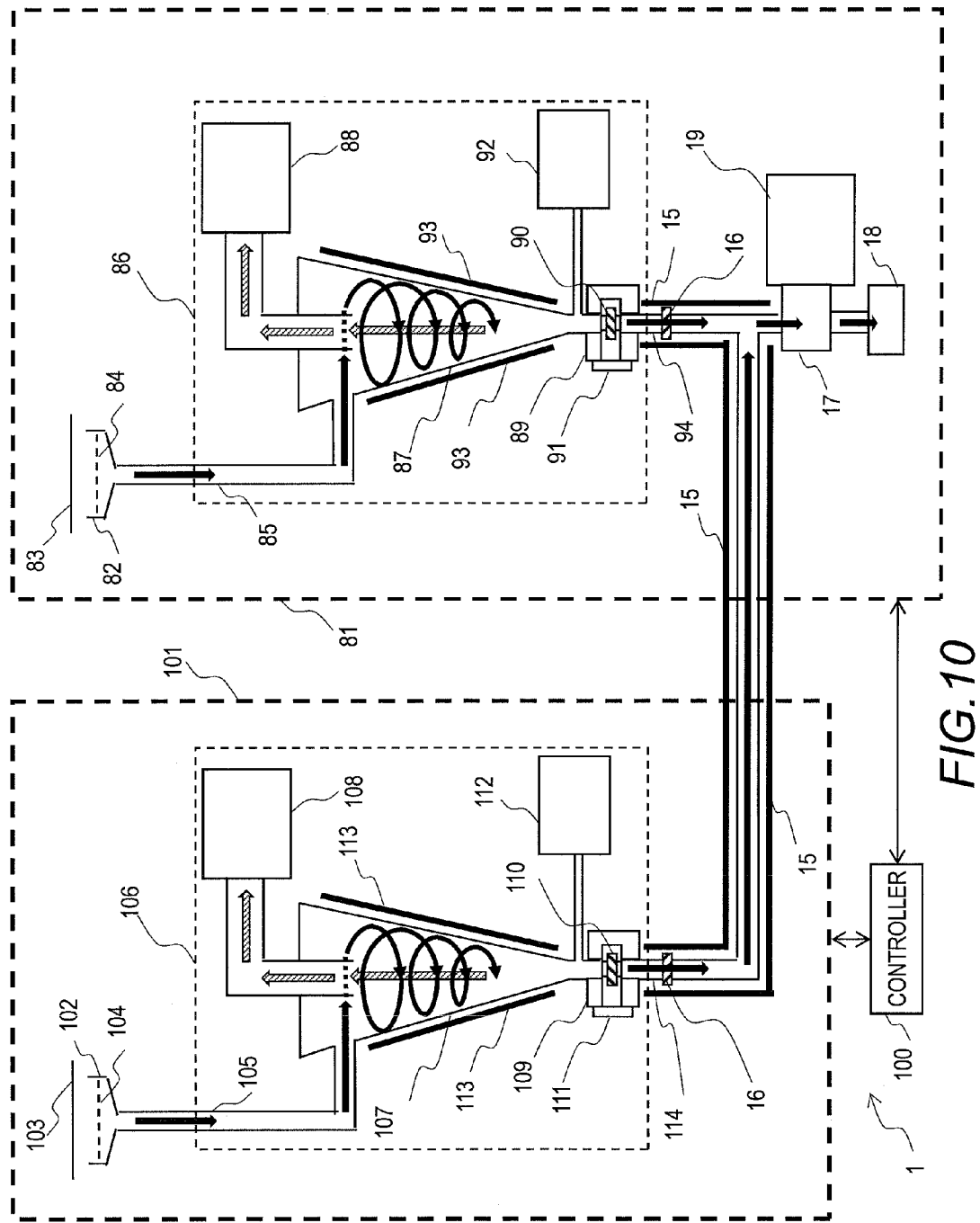
FIG. 10 is a schematic view illustrating an example of a configuration in which a single analysis unit analyzes samples taken at a plurality of sampling points according to the third embodiment.

FIG. 10 is a schematic view illustrating an example of analyzing, by a single analysis unit, samples taken at a plurality of sampling points according to this embodiment. A plurality of sampling devices installed indoors or outdoors collect a gas and/or particle component in air.

The analyzer includes a first sampling device 81 and a second sampling device 101. In the example illustrated in FIG. 10, the gas and/or particle component in air is collected at two sampling points, but in other cases, the gas and/or particle component in air may be collected at two or more sampling points.

The first sampling device 81 includes a first sampling port 82, and a first cover 83 for preventing rain, insects, or the like from entering the first sampling port 82. The first sampling device 81 sucks the gas and/or particles in air, which correspond to a substance to be detected, through the first sampling port 82. The first sampling port 82 is provided with a first rough mesh filter 84. The first rough mesh filter 84 may have a configuration similar to that of the rough mesh filter 4 in the first embodiment. The sucked gas and/or particles in air are introduced into a first particle sampling unit 86 through a first intake pipe 85.

On the other hand, the second sampling device 101 samples the gas and/or particles at a position different from that of the first sampling device 81. The second sampling device 101 includes a second sampling port 102, and a second cover 103 for preventing rain, insects, or the like from entering the second sampling port 102. The gas and/or particles in air, which correspond to the substance to be detected, are sucked through the second sampling port 102.

The second sampling port 102 is provided with a second rough mesh filter 104. The second rough mesh filter 104 may have a structure similar to that of the first rough mesh filter 84. The sucked gas and/or particles in air are introduced into a second particle sampling unit 106 through a second intake pipe 105.

The first particle sampling unit 86 includes a substantially conical first particle holding unit 87, a first large intake pump 88, a first collection heating unit 89, a first particle collection filter 90, a first filter holder 91, a first flow control unit 92, and a first anti-adsorption device 93. The first particle sampling unit 86 operates similarly to the particle sampling unit 6 in the first embodiment, and for example, holds and condenses particles each having a particle diameter of 1 micrometer or more, which rotationally move due to the cyclonic phenomenon, in a space inside the first particle holding unit 87.

The second particle sampling unit 106 includes a substantially conical second particle holding unit 107, a second large intake pump 108, a second collection heating unit 109, a second particle collection filter 110, a second filter holder 111, a second flow control unit 112, and a second anti-adsorption device 113. The second particle sampling unit 106 operates similarly to the particle sampling unit 6 in the first embodiment, and holds and condenses particles each having a specific particle diameter (for example, 1 micrometer or more), which rotationally move due to the cyclonic phenomenon, in a space inside the second particle holding unit 107. The first particle sampling unit 86 and the second particle sampling unit 106 may use a common large intake pump.

The first flow control unit 92 and the second flow control unit 112 can control the settling of the particles held while being rotationally moved in the first particle holding unit 87 and the second particle holding unit 107, respectively.

Specifically, when the first flow control unit 92 reduces the pressure in the lower part of the first particle holding unit 87, the particles each having a particle diameter of 1 micrometer or more, which have rotationally moved in the first particle holding unit 87, settle. The first particle collection filter 90 inside the first filter holder 91 of the first collection heating unit 89 collects the settled particles. The first collection heating unit 89 heats the particles on the first particle collection filter 90.

The particles are heated to vaporize a substance from the particles. The vaporized substance is introduced into the ion source 17 by the intake pump 18 through a first analysis pipe 94. The ion source 17 generates ions from the introduced substance, and the analysis unit 19 analyzes the mass of the ions. The analysis unit 19 measures the mass spectrum to identify the component of the particles and determine the concentration thereof.

With reference to the operational signal of the first flow control unit 92 as a first trigger for the start of analysis, the analysis unit 19 can identify the sample subjected to analysis as a sample obtained from the particles held by the first particle holding unit 87. The operational timing of each of the first flow control unit 92 and the analysis unit 19 is described later with reference to FIG. 12.

Similarly, when the second flow control unit 112 reduces the pressure in the lower part of the second particle holding unit 107, the particles each having a particle diameter of 1 micrometer or more, which have rotationally moved in the second particle holding unit 107, settle. The second particle collection filter 110 inside the second filter holder 111 of the second collection heating unit 109 collects the settled particles. The second collection heating unit 109 heats the particles on the second particle collection filter 110.

The particles are heated to vaporize a substance from the particles. The vaporized substance is introduced into the ion source 17, which is arranged in the first sampling device 81, by the intake pump 18 through a second analysis pipe 114. The ion source 17 generates ions from the introduced substance, and the analysis unit 19 analyzes the mass of the ions. The analysis unit 19 measures the mass spectrum to identify the component of the particles and determine the concentration thereof.

With reference to the operational signal of the second flow control unit 112 as a second trigger for the start of analysis, the analysis unit 19 can identify the sample subjected to analysis as a sample obtained from the particles held by the second particle holding unit 107. The operational timing of each of the second flow control unit 112 and the analysis unit 19 is described later with reference to FIG. 12.

This configuration switches the particle analysis based on the operational signals of the first flow control unit 92 and the second flow control unit 112. Therefore, switching by using a mechanism, such as switching by using a valve, is unnecessary, and influence of adsorption of a sample to the inside of the valve can be avoided.

Figure 11:
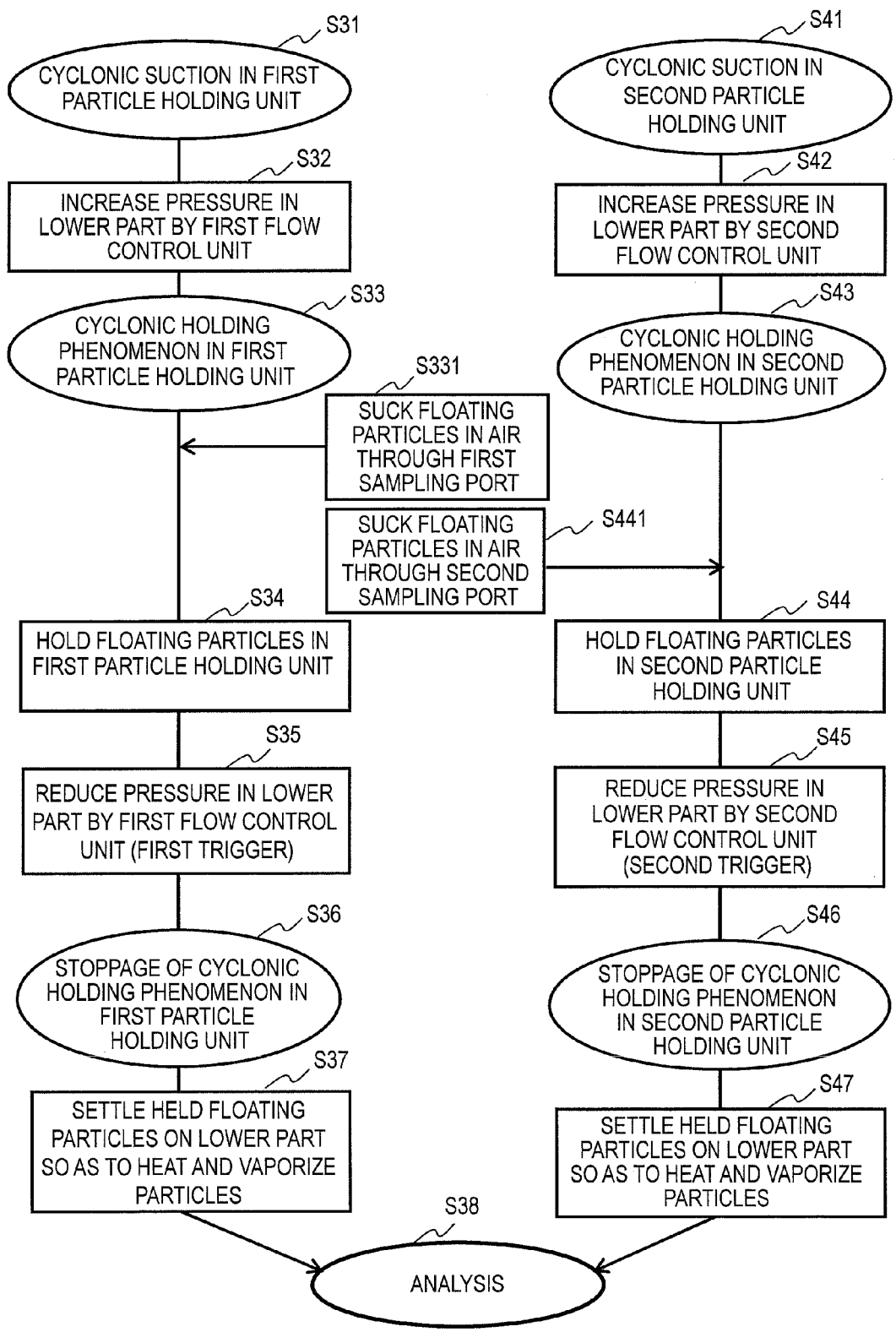
FIG. 11 is a flow chart illustrating an example of a processing procedure of analyzing, by the single analysis unit, the samples taken at the plurality of sampling points according to the third embodiment.

FIG. 11 is a flow chart illustrating an example of processing of analyzing, by the single analysis unit, samples collected at a plurality of sampling points according to this embodiment. The first large intake pump 88 starts suction, and then gas rotational movement corresponding to a cyclonic phenomenon occurs inside the first particle holding unit 87 (Step S31). After that, the first flow control unit 92 increases, in accordance with an instruction from the controller 100, the pressure in the lower part of the first particle holding unit 87 (Step S32). With this, a phenomenon that particles each having a predetermined particle diameter or more are held while being rotationally moved occurs inside the first particle holding unit 87 (Step S33).

The first particle sampling unit 86 sucks, through suction of the first large intake pump 88, air containing a gas and/or particles corresponding to the substance to be detected through the first sampling port 82 (Step S331). Among the floating particles, particles having a specific particle diameter size (for example, particles each having a particle diameter of 1 micrometer or more) are held while being rotated in a space inside the first particle holding unit 87 (Step S34). After the particles are held for a predetermined time period, the first flow control unit 92 reduces, in accordance with an instruction from the controller 100, the pressure in the lower part of the first particle holding unit 87 (Step S35). With this, the phenomenon that the particles are held inside the first particle holding unit 87 stops (Step S36).

The particles having a specific particle diameter size (for example, particles each having a particle diameter of 1 micrometer or more), which have been rotationally held, substantially simultaneously settle on the lower part of the first particle holding unit 87, and the particles are collected by the first particle collection filter 90 of the first collection heating unit 89. The first collection heating unit 89 heats and vaporizes the particles adhering to the first particle collection filter 90 (Step S37). The analysis unit 19 analyzes the vaporized component (Step S38).

On the other hand, the second large intake pump 108 starts suction, and then gas rotational movement corresponding to a cyclonic phenomenon occurs inside the second particle holding unit 107 (Step S41). After that, the second flow control unit 112 increases, in accordance with an instruction from the controller 100, the pressure in the lower part of the second particle holding unit 107 (Step S42). With this, a phenomenon that particles each having a predetermined particle diameter or more are held while being rotationally moved occurs inside the second particle holding unit 107 (Step S43).

The second particle sampling unit 106 sucks, through suction of the second large intake pump 108, air containing a gas and/or particles corresponding to the substance to be detected through the second sampling port 102 (Step S441). Among the floating particles, particles having a specific particle diameter size (for example, particles each having a particle diameter of 1 micrometer or more) are held while being rotated in a space inside the second particle holding unit 107 (Step S44).

After the particles are held for a predetermined time period, the second flow control unit 112 reduces, in accordance with an instruction from the controller 100, the pressure in the lower part of the second particle holding unit 107 (Step S45). With this, the phenomenon that the particles are held inside the second particle holding unit 107 stops (Step S46).

The particles having a specific particle diameter size (for example, particles each having a particle diameter of 1 micrometer or more), which have been rotationally held, substantially simultaneously settle on the lower part of the second particle holding unit 107, and the particles are collected by the second particle collection filter 110 of the second collection heating unit 109. The second collection heating unit 109 heats and vaporizes the particles adhering to the second particle collection filter 110 (Step S47). The analysis unit 19 analyzes the vaporized component (Step S38).

The analysis unit 19 analyzes the component based on a first trigger of the first flow control unit 92 (Step S35) and a second trigger of the second flow control unit 112 (Step S45).

With this, the analysis unit 19 can determine whether the signal of the analysis is a signal based on the particles collected by the first sampling device 81 or a signal based on the particles collected by the second sampling device 101.

Figure 12:
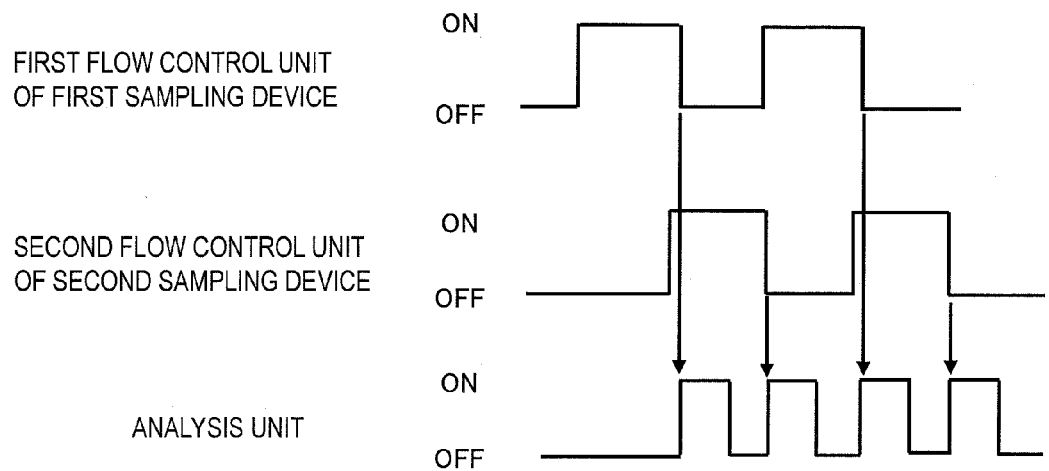
FIG. 12 is a diagram illustrating an example of a sequence of analyzing, by the single analysis unit, the samples taken at the plurality of sampling points according to the third embodiment.

FIG. 12 is a diagram illustrating an example of a sequence of analyzing, by the single analysis unit, samples taken at a plurality of sampling points according to this embodiment. FIG. 12 illustrates the operational signal of the first flow control unit 92 of the first sampling device 81, the operational signal of the second flow control unit 112 of the second sampling device 101, and the operational signal of the analysis unit 19.

The operational signal is a signal representing the operational state of the corresponding element. The operational signals of the first and second flow control units 92 and 112 are transmitted from the first and second flow control units 92 and 112, respectively, or from the controller 100 to the analysis unit 19.

When the operational signal of the first flow control unit 92 is ON, the first flow control unit 92 maintains a high pressure in the lower part of the first particle holding unit 87. During this period, particles are rotationally held inside the first particle holding unit 87. When the operational signal of the first flow control unit 92 is OFF, the first flow control unit 92 maintains a low pressure in the lower part of the first particle holding unit 87.

When the operational signal of the first flow control unit 92 is changed from ON to OFF, the particles that have been rotationally held inside the first particle holding unit 87 settle on the first particle collection filter 90. The analysis unit 19 starts analysis when a predetermined time period (including zero) has elapsed after the operational signal of the first flow control unit 92 is changed to OFF (the operational signal of the analysis unit 19 is ON), and ends the analysis when a predetermined time period has elapsed (the operational signal of the analysis unit 19 is OFF). The analysis unit 19 can analyze the sample heated and vaporized at the first particle collection filter 90.

During a period in which the analysis unit 19 analyzes the sample vaporized from the first particle collection filter 90, the operational signal of the second flow control unit 112 is ON. The operational signal of the second flow control unit 112 is changed to ON before or after the start of the analysis. During a period in which the operational signal of the second flow control unit 112 is ON, particles are rotationally held inside the second particle holding unit 107.

When a predetermined time period (including zero) has elapsed after the operational signal of the analysis unit 19 is changed to OFF, the operational signal of the second flow control unit 112 is changed to OFF. The particles that have been rotationally held inside the second particle holding unit 107 settle and adhere to the second particle collection filter 110.

The analysis unit 19 starts analysis when a predetermined time period (including zero) has elapsed after the operational signal of the second flow control unit 112 is changed to OFF (the operational signal of the analysis unit 19 is ON), and ends the analysis when a predetermined time period has elapsed (the operational signal of the analysis unit 19 is OFF). The analysis unit 19 can analyze the substance heated and vaporized at the second particle collection filter 110.

During a period in which the analysis unit 19 analyzes the sample heated and vaporized at the second particle collection filter 110, the operational signal of the first flow control unit 92 is ON. The operational signal of the first flow control unit 92 is changed to ON before or after the start of the analysis.

The first flow control unit 92, the second flow control unit 112, and the analysis unit 19 repeat those operations to alternately measure and analyze the sample taken by the first sampling device 81 and the sample taken by the second sampling device 101. With this configuration, the single analysis unit can individually analyze samples taken at a plurality of sampling points, and thus the number of components of the analyzer can be reduced.

In this embodiment, samples taken at two sampling points are alternately measured, but in other cases, the samples collected by the first sampling device 81 may be analyzed a plurality of times, and then the samples collected by the second sampling device 101 may be analyzed a plurality of times. The analysis unit 19 alternately repeats the analysis a plurality of times for each sampling device. Further, the second sampling device 101 may hold particles in a time period that overlaps with a time period in which the first sampling device 81 holds particles. Those devices may have different holding time periods.

As described above, the first flow control unit 92 and the second flow control unit 112 respectively cause the particles to settle on the first particle collection filter 90 and the second particle collection filter 110 at different timings. The analysis unit 19 individually analyzes the substances from the first particle collection filter 90 and the second particle collection filter 110 at different timings. A time period from settling of the particles to the end of analysis is shifted between the two sampling devices, and the single analysis unit 19 can individually analyze the substances from the two sampling devices.

Figure 13:
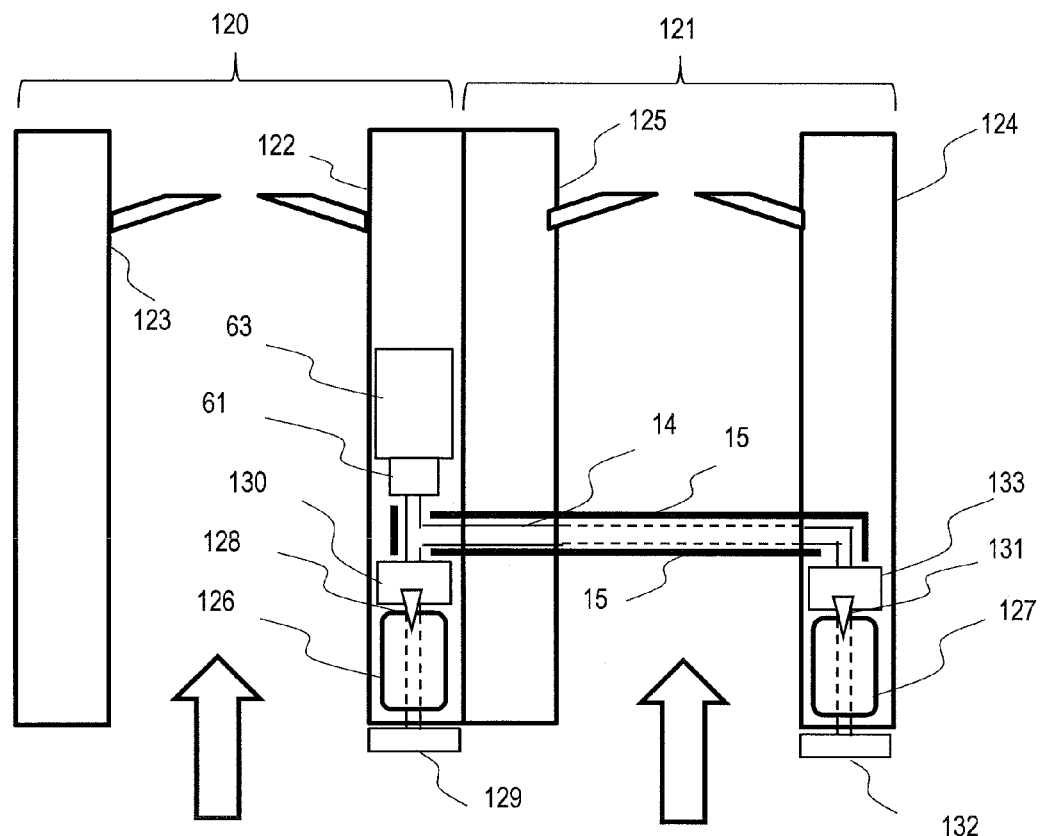
FIG. 13 illustrates a configuration example of security gates according to the third embodiment.

FIG. 13 illustrates an example of a configuration for analyzing, by a single analysis unit embedded in a security gate, samples taken at two one-way security gates according to this embodiment. FIG. 13 illustrates an example in which the security gate incorporates a function of detecting explosive particles, and the single analysis unit is used to operate the two security gates.

FIG. 13 illustrates a configuration of the security gates as viewed from above. A first security gate 120 and a second security gate 121 are present. The first and second security gates 120 and 121 are one-way security gates, and also have the same passage direction. In FIG. 13, the lower side is the entrance, and the upper side is the exit.

The first security gate 120 includes a first master unit 122 having a first authentication plane 126 mounted thereon, and a first auxiliary unit 123 having sensors mounted thereon so as to recognize human passage. The second security gate 121 similarly includes a second master unit 124 having a second authentication plane 127 mounted thereon, and a second auxiliary unit 125.

The first master unit 122 includes the first authentication plane 126, a first blowing unit 128, a first introduction unit 129, a first particle sampling unit 130, the ion source 61, and the analysis unit 63. Although not illustrated, the first master unit 122 also includes a controller for controlling operations of the respective components. The second master unit 124 includes the second authentication plane 127, a second blowing unit 131, a second introduction unit 132, and a second particle sampling unit 133.

The first particle sampling unit 130 and the second particle sampling unit 133 are connected to the ion source 61 and the analysis unit 63 through the analysis pipe 14. The analysis pipe 14 is installed at a position that does not inhibit human passage, such as a position under the floor. The analysis pipe heater 15 heats the analysis pipe 14 to prevent adsorption of a gas to the inside of the analysis pipe 14. For example, the analysis pipe heater 15 heats the analysis pipe 14 at 180° C.

A person who passes through the first security gate 120 brings cards such as an IC card, an entrance and exit card, an employee ID card, a boarding ticket, and an entrance and exit ticket close to the first authentication plane 126. The explosive particles are adhering to those items with high possibility. It should be noted that authentication may be omitted, and the person who passes the security gate may simply place his/her hand or personal item, which is considered to have explosive particles adhering thereon, at a position over the authentication plane 126.

The first blowing unit 128 blows air along the first authentication plane 126 to separate the gas and/or particles corresponding to the substance to be detected that adheres onto the item placed over the first authentication plane 126. The first introduction unit 129 sucks the separated gas and/or particles as the substance to be detected. The sucked particles (including gas adsorbent particles) as the substance to be detected are held and condensed by the first particle sampling unit 130. The first particle sampling unit 130 operates similarly to the first particle sampling unit 86 of the configuration described with reference to FIG. 10.

The first particle sampling unit 130 holds, in accordance with the operation of the flow control unit (not shown), the particles as the substance to be detected in a condensed state while rotationally moving the particles as the substance to be detected for a predetermined time period. The particles held in the first particle sampling unit 130 settle in accordance with the operation of the flow control unit, and are collected on a filter. The particles on the filter are heated so as to vaporize the sample.

The ion source 61 ionizes the heated and vaporized sample. The analysis unit 63 analyzes the mass of the ionized sample. A user or the identification unit 65 determines the presence and absence of the substance to be detected and identifies the detected substance based on the mass spectrometry result.

Also at the second security gate 121, the second blowing unit 131 blows air along the second authentication plane 127 to separate the gas and/or particles corresponding to the substance to be detected that adheres onto the item placed over the second authentication plane 127. The second introduction unit 132 sucks the separated gas and/or particles as the substance to be detected.

The sucked particles (including gas adsorbent particles) as the substance to be detected are held and condensed by the second particle sampling unit 133. The second particle sampling unit 133 operates similarly to the second particle sampling unit 106 of the configuration described with reference to FIG. 10.

The second particle sampling unit 133 holds, in accordance with the operation of the flow control unit (not shown), the particles as the substance to be detected in a condensed state while rotationally moving the particles as the substance to be detected for a predetermined time period. The particles held in the second particle sampling unit 133 settle in accordance with the operation of the flow control unit, and are collected on a filter. The particles on the filter are heated so as to vaporize the sample.

The ion source 61 ionizes the heated and vaporized sample. The analysis unit 63 analyzes the mass of the ionized sample. A user or the identification unit 65 determines the presence and absence of the substance to be detected and identifies the detected substance based on the mass spectrometry result.

As described with reference to FIGS. 10 to 12, the analysis unit 63 starts and ends the analysis depending on the operational signals of the flow control units of the respective first and second particle sampling units 130 and 133. Specifically, the analysis unit 63 uses, as a trigger for the start of analysis, a timing at which the held particles settle in accordance with the operation of the flow control unit in each of the first particle sampling unit 130 and the second particle sampling unit 133.

A timing at which the particles settle and a timing at which the analysis unit 63 analyzes the particles are shifted between the first and second particle sampling units 130 and 133. The analysis unit 63 can individually analyze the samples collected at the respective first security gate 120 and second security gate 121, and further can identify the security gate at which the analysis target is collected.

Figure 14:
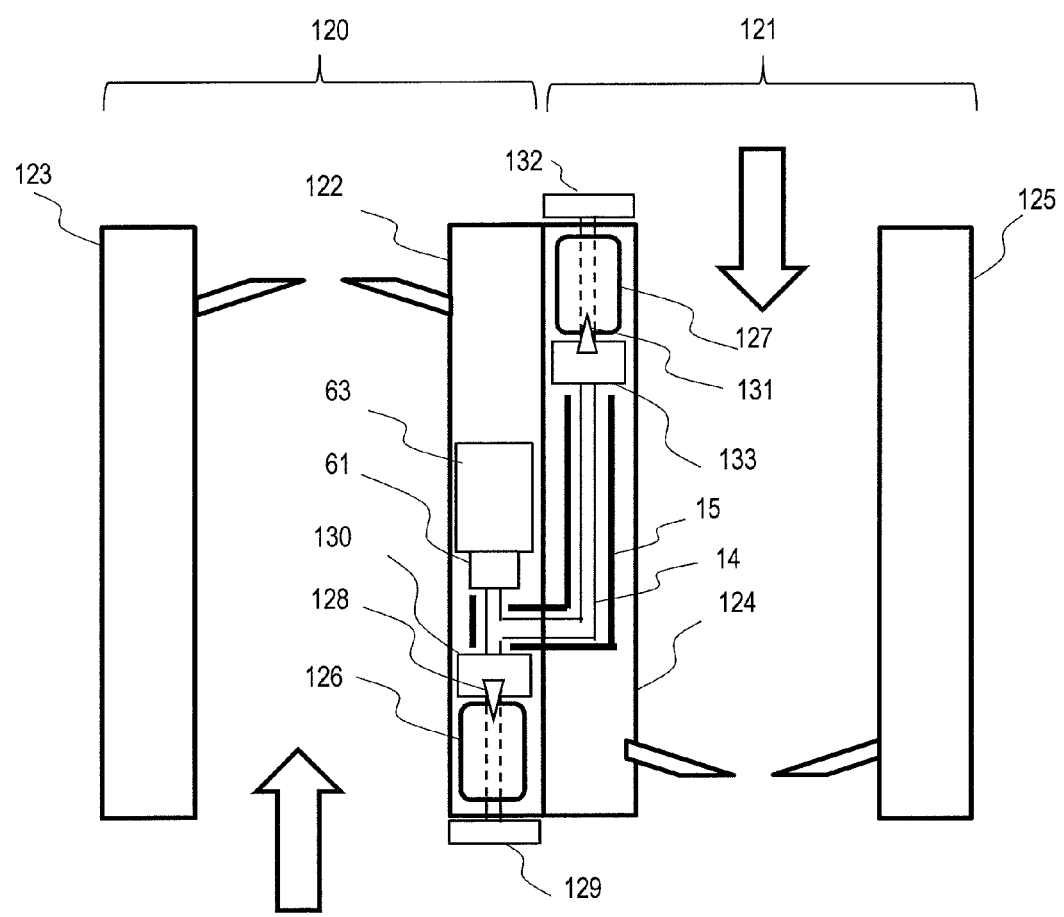
FIG. 14 illustrates another configuration example of the security gates according to the third embodiment.

FIG. 14 illustrates another configuration of the security gates according to this embodiment. In the following, points different from the configuration illustrated in FIG. 13 are described. The direction of the second security gate 121 of this configuration and the passage direction thereof are opposite to those of the second security gate 121 of the configuration illustrated in FIG. 13. The second master unit 124 is installed adjacent to the first master unit 122, and the analysis pipe 14 is installed in, for example, a casing of the first and second security gates 120 and 121. The operations of the respective components of the first and second security gates 120 and 121 in order to collect and analyze the substance to be detected are similar to those of the configuration in FIG. 13.

Figure 15:
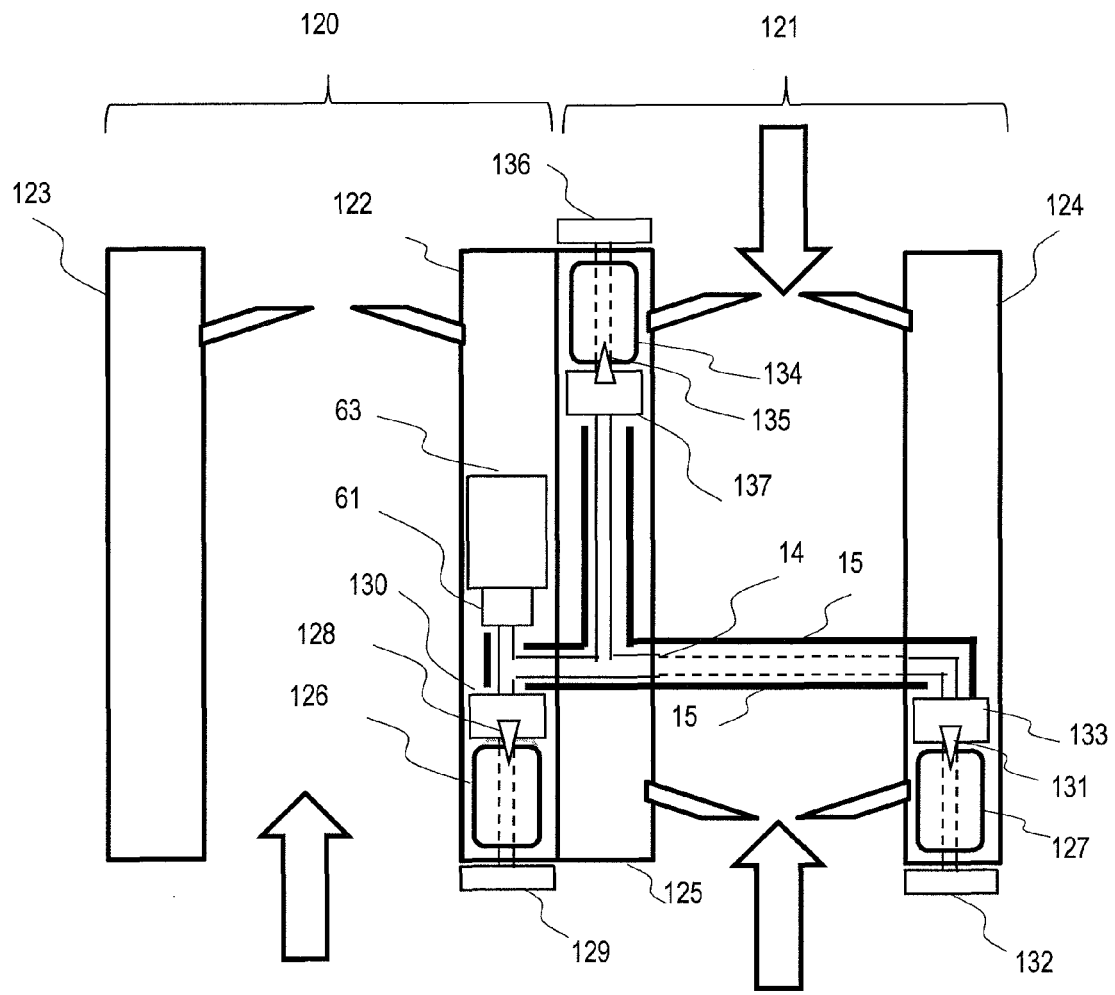
FIG. 15 illustrates another configuration example of the security gates according to the third embodiment.

FIG. 15 illustrates another configuration of the security gates according to this embodiment. In the following, points different from the configuration illustrated in FIG. 13 are described. In the configuration of FIG. 15, the second security gate is a two-way security gate. The second auxiliary unit 125 of the second security gate 121 includes a third authentication plane 134. The second auxiliary unit 125 further includes a third blowing unit 135, a third introduction unit 136, and a third particle sampling unit 137. The first particle sampling unit 130, the second particle sampling unit 133, and the third particle sampling unit 137 are connected to the ion source 61 and the analysis unit 63 through the analysis pipe 14.

At the second security gate 121, the third blowing unit 135 blows air along the third authentication plane 134 to separate the gas and/or particles corresponding to the substance to be detected that adheres onto the item placed over the third authentication plane 134. The third introduction unit 136 sucks the separated gas and/or particles as the substance to be detected.

The sucked particles as the substance to be detected are held and condensed by the third particle sampling unit 137. The third particle sampling unit 137 has a configuration similar to, for example, that of the second particle sampling unit 133, and operates similarly to the second particle sampling unit 133. The substance to be detected that is collected by the third particle sampling unit 137 is heated and vaporized to be ionized by the ion source 61, and then the ions are analyzed by the analysis unit 63.

The analysis unit 63 starts and ends the analysis depending on the operational signals of the flow control units of the respective first, second, and third particle sampling units 130, 133, and 137. Specifically, the analysis unit 63 uses, as a trigger for the start of analysis, a timing at which the held particles settle in accordance with the operation of the flow control unit in each of the first, second, and third particle sampling units 130, 133, and 137.

A timing at which the particles settle and a timing at which the analysis unit 63 analyzes the particles are shifted among the first, second, and third particle sampling units 130, 133, and 137. The analysis unit 63 can individually analyze the samples collected at the different security gates, and further can identify the security gate at which the analysis target is collected.

Figure 16:
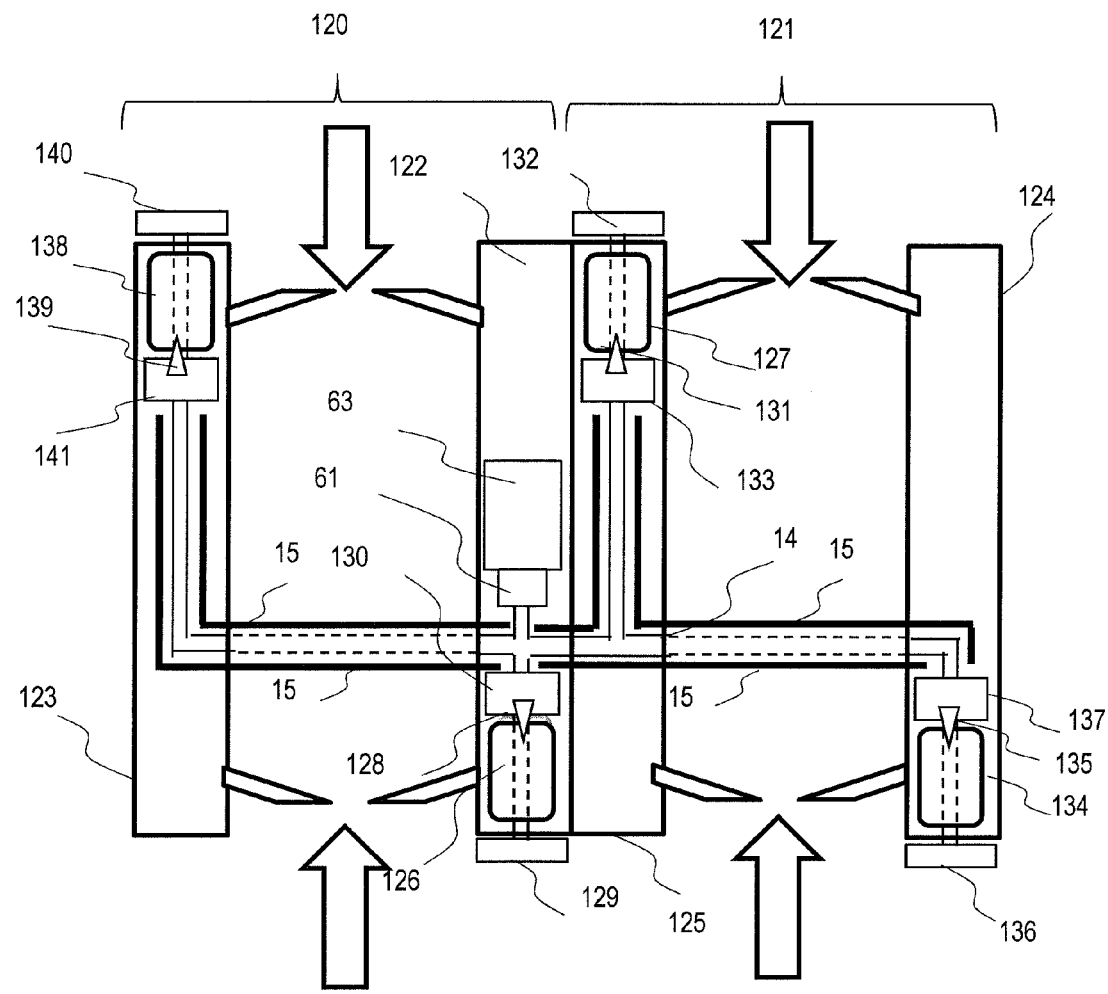
FIG. 16 illustrates another configuration example of the security gates according to the third embodiment.

FIG. 16 illustrates another configuration of the security gates according to this embodiment. In the following, points different from the configuration illustrated in FIG. 15 are described. The first security gate 120 is a two-way security gate. The first auxiliary unit 123 includes a fourth authentication plane 138. The first auxiliary unit 123 further includes a fourth blowing unit 139, a fourth introduction unit 140, and a fourth particle sampling unit 141. The fourth particle sampling unit 141 is connected to the ion source 61 and the analysis unit 63 through the analysis pipe 14.

At the first security gate 120, the fourth blowing unit 139 blows air along the fourth authentication plane 138 to separate the gas and/or particles corresponding to the substance to be detected that adheres onto the item placed over the fourth authentication plane 138. The fourth introduction unit 140 sucks the separated gas and/or particles as the substance to be detected.

The sucked particles as the substance to be detected are held and condensed by the fourth particle sampling unit 141. The fourth particle sampling unit 141 has a configuration similar to, for example, that of the first particle sampling unit 130, and operates similarly to the first particle sampling unit 130. The substance to be detected that is collected by the fourth particle sampling unit 141 is heated and vaporized to be ionized by the ion source 61, and then the ions are analyzed by the analysis unit 63.

The analysis unit 63 starts and ends the analysis depending on the operational signals of the flow control units of the respective first to fourth particle sampling units 130, 133, 137, and 141. Specifically, the analysis unit 63 uses, as a trigger for the start of analysis, a timing at which the held particles settle in accordance with the operation of the flow control unit in each of the first to fourth particle sampling units 130, 133, 137, and 141.

A timing at which the particles settle and a timing at which the analysis unit 63 analyzes the particles are shifted among the first to fourth particle sampling units 130, 133, 137, and 141. The analysis unit 63 can individually analyze the samples collected at the different security gates, and further can identify the security gate at which the analysis target is collected.

Fourth Embodiment

Now, a fourth embodiment of this invention is described. In this embodiment, the particle sampling unit uses a plurality of particle holding units to collect the particles. With this, the particle diameter of particles to be held and collected as the substance to be detected can be controlled. In the following, a difference from the first embodiment is mainly described.

Figure 17:
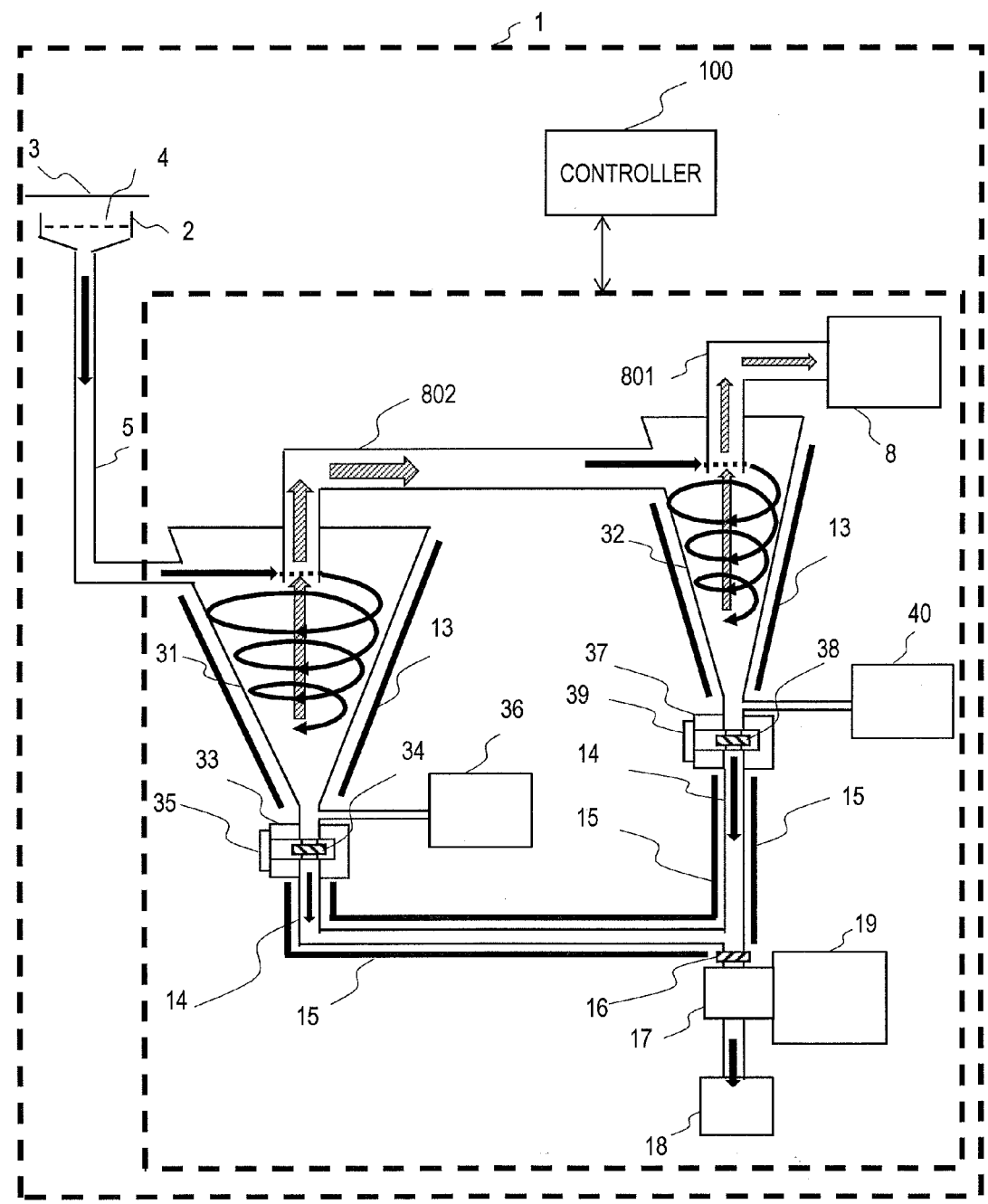
FIG. 17 is a view illustrating a configuration example of an analyzer that uses a large rotation particle holding unit and a small rotation particle holding unit according to a fourth embodiment of this invention.

FIG. 17 illustrates a configuration example of an analyzer that uses two particle holding units according to this embodiment. Particle holding units 31 and 32 have different separation limit particle diameters. The separation limit particle diameter of the particle holding unit 32 is smaller than the separation limit particle diameter of the particle holding unit 31. The particle holding unit 32 can collect particles having a particle diameter smaller than that of the particles to be collected by the particle holding unit 31.

In the example of FIG. 17, the large rotation particle holding unit 31 and the small rotation particle holding unit 32 each have a substantially conical shape. The maximum rotational radius of particles to be separated by the cyclonic phenomenon in the large rotation particle holding unit 31 is larger than the maximum rotational radius of particles to be separated by the cyclonic phenomenon in the small rotation particle holding unit 32. The large intake pump 8 sucks air for both of the small rotation particle holding unit 32 and the large rotation particle holding unit 31.

In the example of FIG. 17, in a region between the sampling port 2 and the large intake pump 8, the large rotation particle holding unit 31 and the small rotation particle holding unit 32 are connected to each other in series. An intake pipe 802 is connected to a top part of the large rotation particle holding unit 31 and a side wall of the small rotation particle holding unit 32. The large intake pump 8 sucks air inside the large rotation particle holding unit 31 through the small rotation particle holding unit 32. The intake pipe 802 causes the cyclonic phenomenon through suction of air inside the large rotation particle holding unit 31, and further supplies a sample to the small rotation particle holding unit 32.

The gas and/or particles in air sucked through the sampling port 2 are introduced into the large rotation particle holding unit 31 through the intake pipe 5. The large rotation particle holding unit 31 is provided with a large rotation collection heating unit 33, a large rotation particle collection filter 34, a large rotation filter holder 35, a large rotation flow control unit 36, and the anti-adsorption device 13.

The maximum rotational radius of the large rotation particle holding unit 31 is larger, and hence the large rotation particle holding unit 31 rotationally holds particles each having a larger particle diameter. When the cyclonic phenomenon occurs inside the large rotation particle holding unit 31, for example, particles each having a particle diameter of 10 micrometers or more rotationally move inside the large rotation particle holding unit 31.

The large rotation flow control unit 36 controls a pressure in the lower part of the large rotation particle holding unit 31, and maintains the particles each having a particle diameter of 10 micrometers or more in a space inside the large rotation particle holding unit 31 without settling the particles. The particles each having a particle diameter of 10 micrometers or more are held and condensed while being rotationally moved inside the large rotation particle holding unit 31.

On the other hand, the particles each having a particle diameter of less than 10 micrometers are discharged from the top part of the large rotation particle holding unit 31 through the intake pipe 802 to be introduced into the small rotation particle holding unit 32. The small rotation particle holding unit 32 is provided with a small rotation collection heating unit 37, a small rotation particle collection filter 38, a small rotation filter holder 39, a small rotation flow control unit 40, and the anti-adsorption device 13.

The maximum rotational radius of the small rotation particle holding unit 32 is smaller, and hence the small rotation particle holding unit 32 rotationally holds particles each having a smaller particle diameter. For example, the particles each having a particle diameter of 1 micrometer or more rotationally move inside the small rotation particle holding unit 32. If all of the particles each having a particle diameter of 10 micrometers or more are collected by the large rotation particle holding unit 31, particles each having a particle diameter of 1 micrometer or more and less than 10 micrometers rotationally move inside the small rotation particle holding unit 32.

The small rotation flow control unit 40 adjusts a pressure in the lower part of the small rotation particle holding unit 32, and rotates the particles each having a particle diameter of 1 micrometer or more inside the small rotation particle holding unit 32 without settling the particles. The particles each having a particle diameter of 1 micrometer or more are held and condensed while being rotationally moved in a space inside the small rotation particle holding unit 32. The particles each having a particle diameter of less than 1 micrometer are not held inside the small rotation particle holding unit 32, and are discharged by the large intake pump 8.

The large rotation flow control unit 36 can control the settling of the particles held while being rotationally moved inside the large rotation particle holding unit 31. Similarly, the small rotation flow control unit 40 can control the settling of the particles held while being rotationally moved inside the small rotation particle holding unit 32.

Specifically, the large rotation flow control unit 36 reduces the pressure in the lower part of the large rotation particle holding unit 31 to settle the held and condensed particles each having a particle diameter of 10 micrometers or more. The particles each having a particle diameter of 10 micrometers or more adhere on the large rotation particle collection filter 34 inside the large rotation filter holder 35 of the large rotation collection heating unit 33. The large rotation collection heating unit 33 heats and vaporizes the particles on the large rotation particle collection filter 34.

The analysis pipe 14 is connected to the back surface of the large rotation particle collection filter 34. The heated and vaporized sample is introduced into the ion source 17 by the intake pump 18 through the analysis pipe 14. The analysis unit 19 analyzes the mass of ions generated from the sample by the ion source 17. The analysis unit 19 measures the mass spectrum to identify the component of the particles and determine the concentration thereof based on the mass spectrum.

For example, the analysis unit 19 starts the analysis in response to the operational signal of the large rotation flow control unit 36 as a trigger. Specifically, the analysis unit 19 monitors the operational signal of the large rotation flow control unit 36 and starts the analysis when the analysis unit 19 detects that the large rotation flow control unit 36 has reduced the flow rate to settle the particles. As described above, the analysis unit 19 can determine, based on the operational signal of the large rotation flow control unit 36, that the substance subjected to analysis is a substance from the particles held by the large rotation particle holding unit 31.

The controller 100 may control the large rotation flow control unit 36 or monitor the operational signal of the large rotation flow control unit 36, and instruct the analysis unit 19 to perform analysis in accordance with the control. The analysis unit 19 can determine, in accordance with the instruction from the controller 100, that the substance subjected to analysis is a substance from the particles held by the large rotation particle holding unit 31.

On the other hand, particles each having a particle diameter of 1 to 10 micrometers, which have been held and condensed while being rotationally moved in the small rotation particle holding unit 32, settle through control of the pressure in the lower part of the small rotation particle holding unit 32 by the small rotation flow control unit 40. The small rotation particle collection filter 38 inside the small rotation filter holder 39 of the small rotation collection heating unit 37 collects the particles each having a particle diameter of 1 to 10 micrometers. The small rotation collection heating unit 37 heats and vaporizes the particles on the small rotation particle collection filter 38. The vaporized sample is introduced into the ion source 17 by the intake pump 18 through the analysis pipe 14.

The small rotation flow control unit 40 reduces the flow rate when a predetermined time period has elapsed after the large rotation flow control unit 36 reduces the flow rate, to thereby reduce the pressure in the lower part of the small rotation particle holding unit 32. With this, the analysis unit 19 can individually analyze the substances of particles having different particle diameters.

The analysis unit 19 analyzes, similarly to the analysis of particles held by the large rotation particle holding unit 31, particles held by the small rotation particle holding unit 32. The analysis unit 19 starts the analysis in response to the operational signal of the small rotation flow control unit 40 as a trigger or in accordance with an instruction from the controller 100. With this, the analysis unit 19 can determine that the substance subjected to analysis is a substance from the particles held by the small rotation particle holding unit 32.

According to this embodiment, particles having different particle diameters in air can be separated from each other to be vaporized and analyzed individually. In the above-mentioned embodiment, particles in different particle diameter ranges are separated from each other in different particle holding units to be analyzed individually. A similar method can be applied to analysis for a gas with use of adsorbent particles. For example, the analyzer 1 prepares adsorbent particles of different types with respect to gases of different types to be analyzed. Further, the adsorbent particles of different types have different particle diameters. The supply unit 20 described in the second embodiment supplies the adsorbent particles of the plurality of types.

The large rotation particle holding unit 31 separates adsorbent particles having a larger particle diameter, and the small rotation particle holding unit 32 separates adsorbent particles having a smaller particle diameter. Similarly to the above-mentioned embodiment, the analysis unit 19 individually analyzes a gas or particles adsorbed to the adsorbent particles of different types.

The number of stages of the particle holding units connected to each other in series may be 3 or more. As long as the particle holding units connected to each other in series have different separation limit particle diameters, any value in the configuration may differ among the particle holding units.

This invention is not limited to the above-described embodiments but includes various modifications. The above-described embodiments are explained in details for better understanding of this invention and are not limited to those including all the configurations described above. A part of the configuration of one embodiment may be replaced with that of another embodiment; the configuration of one embodiment may be incorporated to the configuration of another embodiment. A part of the configuration of each embodiment may be added, deleted, or replaced by that of a different configuration.

The above-described configurations, functions, processing units, and processing means, for all or a part of them, may be implemented by hardware: for example, by designing an integrated circuit. The above-described configurations and functions may be implemented by software, which means that a processor interprets and executes programs providing the functions. The information of programs, tables, and files to implement the functions may be stored in a storage device such as a memory, a hard disk drive, or an SSD (Solid State Drive), or a storage medium such as an IC card, or an SD card.

What is claimed is:

1. An analyzer for a substance, comprising:
a first particle holding unit having a tubular shape;
a first intake pipe for sucking a gas from an upper side of the first particle holding unit to cause a cyclonic phenomenon inside the first particle holding unit;
a first supply pipe for supplying a sample containing particles, the first supply pipe being connected to a side surface of the first particle holding unit;
a first flow control unit for controlling a flow rate of a gas flowing into the first particle holding unit to hold the rotationally moving particles inside the first particle holding unit for a predetermined time period so as to condense the particles and then reduce the flow rate of the gas flowing into the first particle holding unit to cause the particles to settle, the first flow control unit being connected to a lower part of the first particle holding unit;
a first collection heating unit for collecting and heating the settled particles; and
an analysis unit for analyzing a substance vaporized from the particles through the heating by the first collection heating unit, the analysis unit being connected to the first collection heating unit through a pipe.

2. The analyzer according to claim 1, further comprising a supply unit for supplying, into the first particle holding unit, adsorbent particles for adsorbing a substance to be analyzed,
wherein the particles contained in the sample comprise the adsorbent particles, and
wherein the first collection heating unit vaporizes the substance to be analyzed from the collected adsorbent particles.

3. The analyzer according to claim 1,
wherein the first flow control unit reduces, in a stepwise manner, the flow rate of the gas flowing into the first particle holding unit, and
wherein the analysis unit analyzes, in each of a plurality of stages of reduction of the flow rate of the gas, the substance vaporized from the particles settling on the first collection heating unit.

4. The analyzer according to claim 1, further comprising:
a second particle holding unit having a tubular shape;
a second intake pipe for sucking a gas from an upper side of the second particle holding unit to cause a cyclonic phenomenon inside the second particle holding unit;
a second supply pipe for supplying a sample containing particles, the second supply pipe being connected to a side surface of the second particle holding unit;
a second flow control unit for controlling a flow rate of a gas flowing into the second particle holding unit to hold the rotationally moving particles inside the second particle holding unit for a predetermined time period and then cause the particles to settle, the second flow control unit being connected to a lower part of the second particle holding unit; and
a second collection heating unit for collecting and heating the particles settled on the second particle holding unit,
wherein the first flow control unit and the second flow control unit cause the particles to settle on the first collection heating unit and the second collection heating unit, respectively, at different timings, and
wherein the analysis unit is connected to the first collection heating unit and the second collection heating unit through the pipe, and analyzes the substance vaporized in the first collection heating unit and the substance vaporized in the second collection heating unit at different timings.

5. The analyzer according to claim 4, wherein the first supply pipe and the second supply pipe supply, to the first particle holding unit and the second particle holding unit, samples taken at different sampling positions, respectively.

6. The analyzer according to claim 4,
wherein the first particle holding unit has a separation limit particle diameter larger than a separation limit particle diameter of the second particle holding unit, and
wherein the second supply pipe supplies, to the second particle holding unit, the sample fed through the first intake pipe.

7. The analyzer according to claim 1,
wherein the first particle holding unit has a tapered side wall having a diameter that reduces toward a lower side thereof, and
wherein the first flow control unit holds the rotationally moving particles inside the first particle holding unit for 0.1 second or more, and then causes the particles to settle.

8. A method of analyzing a substance, the method comprising:
sucking a gas from an upper side of a particle holding unit having a tubular shape to cause a cyclonic phenomenon inside the particle holding unit;
supplying a sample through a side surface of the particle holding unit;
controlling, at a lower part of the particle holding unit, a flow rate of a gas flowing into the particle holding unit to hold rotationally moving particles inside the particle holding unit for a predetermined time period so as to condense the particles and then reduce the flow rate of the gas flowing into the first particle holding unit to cause the particles to settle;
collecting and heating the settled particles; and
analyzing a substance vaporized from the particles through the heating.

* * * * *